US007582428B2

(12) United States Patent
Glenn et al.

(10) Patent No.: US 7,582,428 B2
(45) Date of Patent: Sep. 1, 2009

(54) METHODS AND COMPOSITIONS FOR IDENTIFYING ANTI-HCV AGENTS

(75) Inventors: Jeffrey S. Glenn, Palo Alto, CA (US); Shirit Einav, Stanford, CA (US); Menashe Elazar, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/528,377

(22) PCT Filed: Aug. 18, 2004

(86) PCT No.: PCT/US2004/027070

§ 371 (c)(1), (2), (4) Date: Jan. 14, 2006

(87) PCT Pub. No.: WO2005/032329

PCT Pub. Date: Apr. 14, 2005

(65) Prior Publication Data

US 2006/0199174 A1 Sep. 7, 2006

Related U.S. Application Data

(60) Provisional application No. 60/497,124, filed on Aug. 22, 2003.

(51) Int. Cl.
*C12Q 1/68* (2006.01)
*C12Q 1/00* (2006.01)

(52) U.S. Cl. .................................... 435/6; 435/4; 435/5

(58) Field of Classification Search ....................... None
See application file for complete search history.

(56) References Cited

U.S. PATENT DOCUMENTS

| | | | | |
|---|---|---|---|---|
| 6,020,149 | A | 2/2000 | Fuller-Pace et al. | |
| 2002/0098202 | A1 * | 7/2002 | Wimmer et al. | 424/225.1 |
| 2003/0087873 | A1 | 5/2003 | Stuyver et al. | |

FOREIGN PATENT DOCUMENTS

| | | |
|---|---|---|
| WO | WO 99/01582 | 1/1999 |
| WO | WO 03/073989 | 9/2003 |

OTHER PUBLICATIONS

Jin et al., "Expression, isolation, and characterization of the hepatitis C virus ATPase/RNA helicase," Archives of biochemistry and biophysics, vol. 323 No. 1, pp. 47-53 (Oct. 1995).*
Kadaré et al., "ATPase, GTPase, and RNA binding activities associated with the 206- kilodalton protein of turnip yellow mosaic virus," Journal of Virology, vol. 70 No. 11, pp. 8169-8174 (Nov. 1996).*
Lindström et al., "Mutations of the Hepatitis C virus protein NS4B on either side of the ER membrane affect the efficiency of subgenomic replicons," Virus Resaerch, vol. 121 No. 2, pp. 169-178 (Nov. 2006).*
Morouianu et al, "Protein Export from the Nucleus Requires the GTPase Ran and GTP Hydrolysis," Proceedings of the National Academy of Sciences of the United States of America, vol. 92 No. 10, pp. 4318-4322 (May 1995).*
Rodriguez et al., "Poliovirus protein 2C has ATPase and GTPase activities," Journal of Biological Chemsitry, vol. 268 No. 11, pp. 8105-5110 (Apr. 1993).*
Umareddy et al., "Dengue virus NS4B interacts with NS3 and dissociates it from single-stranded RNA," Journal of General Virology, vol. 87 No. 9, pp. 2605-2614 (Sep. 2006).*
Rosenberg, Recent advances in the molecular biology of Hepatitis C Virus, (2001), J. Mol. Biol., 313(3):451-64.
Kato, Molecular Biology of Hepatitis C Virus, (2001), Acta. Med. Okayama, vol. 55. No. 3, pp. 133-159.
Pfister et al., Characterization of the Nucleoside Triphosphatase activity of Polio Virus Protein 2C reveals a mechanism by which guanidine inhibits Poliovirus replication, J. Biol. Chem., 274(11), 6992-7001, 1999.
Umezu et al., *Escherichia coli* RecQ protein is a DNA helicase, PNAS 87:5363-5367, 1990.
Tate et al., Nucleotide specificity of Cardiac Sarcoplasmic Reticulum, J. Biol. Chem, 266, 24, 16165-16170, 1991.

* cited by examiner

*Primary Examiner*—Zachariah Lucas
(74) *Attorney, Agent, or Firm*—Bozicevic, Field & Francis LLP; James S. Keddie

(57) ABSTRACT

The invention provides methods and compositions for identifying agents for treating infection by viruses that encode a nucleotide-binding NS4B protein, or functional equivalent thereof, e.g., hepatitis C virus (HCV) or other members of the family Flaviviridae. In general, the methods involve contacting an NS4B nucleotide binding motif (NBM)-containing polypeptide with a candidate agent, and determining the effect of the candidate agent on nucleotide binding activity, a nucleotide hydrolyzing activity, or a nucleotide-dependent RNA binding activity of the polypeptide. A candidate agent that inhibits NS4B polypeptide binding to a nucleotide is an anti-viral agent, e.g., an anti-HCV agent. The invention also features a polynucleotide encoding a NS4B polypeptide having a modified NBM (e.g., which is impaired in NTP binding). The subject methods and compositions find use in a variety of therapeutic and screening applications.

6 Claims, 9 Drawing Sheets

Fig .1A

| G protein | A motif | G | PM 2 | B motif |
|---|---|---|---|---|
| Consensus | GXXXXGK(S/T) | F | T | DXXG |
| Ras family: | | | | |
| RAS | GXGGVGKS | F | T | DTAG |
| RHO | GDGAXGKT | F/Y | T | DTAG |
| YPT (Rab) | GXXXXGK(S/T) | F/Y | T | DTAG |
| ARF's: | GL DAAGKT | | T | DVGG |
| EFT: | GHVDHGKT | | T | DCPG |

Fig .1B

| Virus/Protein | A motif | B motif |
|---|---|---|
| Consensus | GXXXXGK(S/T) | D/E |
| P4 Phage/P4α | GP GGSGKS | D |
| HAV/2C | GKRGGGKS | DD |
| Polio/2C | GS PG TGKS | MDD |
| BPV/NS1 | GP AS TGKT | EE |
| CPMV/P58 | GKS R TGKS | DD |
| RHDV/2C | GAP G I GKT | DE |

Fig .1C

| HCV/NS4B1 | A motif | G | PM2 | B motif |
|---|---|---|---|---|
| Consensus | GSIGL**GK** | F | T | DAAA |
| Genotype 1b | GSIGL**GK** | F | T | DAAA |
| Genotype 3 | GSIGL**G**<u>**R**</u> | F | T | DAAA |
| G129V | <u>V</u>SIGL**GK** | F | T | DAAA |
| I131N | GS<u>N</u>GL**GK** | F | T | DAAA |
| K135S | GSIGL**G**<u>**S**</u> | F | T | DAAA |
| K135R | GSIGL**G**<u>**R**</u> | F | T | DAAA |

Fig. 6A

| | | | | | | | |
|---|---|---|---|---|---|---|---|
| NBM protein consensus | G | X1 | X2 | X3 | X4 | G | K |
| NS4B consensus: | G | S | I | G | L | G | K |
| Genotype 1b: | G | S | I | G | L | G | K |

Fig. 6B

Engineered mutations in HCV replicon

| | | | | | | |
|---|---|---|---|---|---|---|
| V | S | I | G | L | G | K (G129V) |
| G | S | N | G | L | G | K (I131N) |
| G | S | I | G | L | G | **S** (K135S) |
| G | S | I | G | L | G | **R** (K135R) |

Location of motifs A and B of NS4B's NBM

SEQUENCE LISTING

```
<160> NUMBER OF SEQ ID NOS: 42

<210> SEQ ID NO 1
<211> LENGTH: 8
<212> TYPE: PRT
<213> ORGANISM: artificial sequence
<220> FEATURE:
<223> OTHER INFORMATION: synthetic polymer
<220> FEATURE:
<221> NAME/KEY: VARIANT
<222> LOCATION: 2
<223> OTHER INFORMATION: Xaa = Any Amino Acid

<400> SEQUENCE: 1

Gly Xaa Gly Gly Val Gly Lys Ser
 1               5


<210> SEQ ID NO 2
<211> LENGTH: 8
<212> TYPE: PRT
<213> ORGANISM: artificial sequence
<220> FEATURE:
<223> OTHER INFORMATION: synthetic polymer
<220> FEATURE:
<221> NAME/KEY: VARIANT
<222> LOCATION: 5
<223> OTHER INFORMATION: Xaa = Any Amino Acid

<400> SEQUENCE: 2

Gly Asp Gly Ala Xaa Gly Lys Thr
 1               5


<210> SEQ ID NO 3
<211> LENGTH: 8
<212> TYPE: PRT
<213> ORGANISM: artificial sequence
<220> FEATURE:
<223> OTHER INFORMATION: synthetic polymer

<400> SEQUENCE: 3

Gly Leu Asp Ala Ala Gly Lys Thr
 1               5


<210> SEQ ID NO 4
<211> LENGTH: 8
<212> TYPE: PRT
<213> ORGANISM: artificial sequence
<220> FEATURE:
<223> OTHER INFORMATION: synthetic polymer

<400> SEQUENCE: 4

Gly His Val Asp His Gly Lys Thr
 1               5
```

-continued

```
<210> SEQ ID NO 5
<211> LENGTH: 4
<212> TYPE: PRT
<213> ORGANISM: artificial sequence
<220> FEATURE:
<223> OTHER INFORMATION: synthetic polymer

<400> SEQUENCE: 5

Asp Thr Ala Gly
 1


<210> SEQ ID NO 6
<211> LENGTH: 4
<212> TYPE: PRT
<213> ORGANISM: artificial sequence
<220> FEATURE:
<223> OTHER INFORMATION: synthetic polymer

<400> SEQUENCE: 6

Asp Val Gly Gly
 1


<210> SEQ ID NO 7
<211> LENGTH: 4
<212> TYPE: PRT
<213> ORGANISM: artificial sequence
<220> FEATURE:
<223> OTHER INFORMATION: synthetic polymer

<400> SEQUENCE: 7

Asp Cys Pro Gly
 1


<210> SEQ ID NO 8
<211> LENGTH: 8
<212> TYPE: PRT
<213> ORGANISM: artificial sequence
<220> FEATURE:
<223> OTHER INFORMATION: synthetic polymer

<400> SEQUENCE: 8

Gly Pro Gly Gly Ser Gly Lys Ser
 1               5


<210> SEQ ID NO 9
<211> LENGTH: 8
<212> TYPE: PRT
<213> ORGANISM: artificial sequence
<220> FEATURE:
<223> OTHER INFORMATION: synthetic polymer

<400> SEQUENCE: 9

Gly Lys Arg Gly Gly Gly Lys Ser
 1               5


<210> SEQ ID NO 10
<211> LENGTH: 8
<212> TYPE: PRT
<213> ORGANISM: artificial sequence
<220> FEATURE:
<223> OTHER INFORMATION: synthetic polymer

<400> SEQUENCE: 10

Gly Ser Pro Gly Thr Gly Lys Ser
 1               5


<210> SEQ ID NO 11
```

-continued

<211> LENGTH: 8
<212> TYPE: PRT
<213> ORGANISM: artificial sequence
<220> FEATURE:
<223> OTHER INFORMATION: synthetic polymer

<400> SEQUENCE: 11

Gly Pro Ala Ser Thr Gly Lys Thr
1 5

<210> SEQ ID NO 12
<211> LENGTH: 8
<212> TYPE: PRT
<213> ORGANISM: artificial sequence
<220> FEATURE:
<223> OTHER INFORMATION: synthetic polymer

<400> SEQUENCE: 12

Gly Lys Ser Arg Thr Gly Lys Ser
1 5

<210> SEQ ID NO 13
<211> LENGTH: 8
<212> TYPE: PRT
<213> ORGANISM: artificial sequence
<220> FEATURE:
<223> OTHER INFORMATION: synthetic polymer

<400> SEQUENCE: 13

Gly Ala Pro Gly Ile Gly Lys Thr
1 5

<210> SEQ ID NO 14
<211> LENGTH: 7
<212> TYPE: PRT
<213> ORGANISM: artificial sequence
<220> FEATURE:
<223> OTHER INFORMATION: synthetic polymer

<400> SEQUENCE: 14

Gly Ser Ile Gly Leu Gly Lys
1 5

<210> SEQ ID NO 15
<211> LENGTH: 7
<212> TYPE: PRT
<213> ORGANISM: artificial sequence
<220> FEATURE:
<223> OTHER INFORMATION: synthetic polymer

<400> SEQUENCE: 15

Gly Ser Ile Gly Leu Gly Arg
1 5

<210> SEQ ID NO 16
<211> LENGTH: 7
<212> TYPE: PRT
<213> ORGANISM: artificial sequence
<220> FEATURE:
<223> OTHER INFORMATION: synthetic polymer

<400> SEQUENCE: 16

Val Ser Ile Gly Leu Gly Lys
1 5

<210> SEQ ID NO 17
<211> LENGTH: 7

-continued

```
<212> TYPE: PRT
<213> ORGANISM: artificial sequence
<220> FEATURE:
<223> OTHER INFORMATION: synthetic polymer

<400> SEQUENCE: 17

Gly Ser Asn Gly Leu Gly Lys
 1               5


<210> SEQ ID NO 18
<211> LENGTH: 7
<212> TYPE: PRT
<213> ORGANISM: artificial sequence
<220> FEATURE:
<223> OTHER INFORMATION: synthetic polymer

<400> SEQUENCE: 18

Gly Ser Ile Gly Leu Gly Ser
 1               5


<210> SEQ ID NO 19
<211> LENGTH: 7
<212> TYPE: PRT
<213> ORGANISM: artificial sequence
<220> FEATURE:
<223> OTHER INFORMATION: synthetic polymer

<400> SEQUENCE: 19

Gly Ser Ile Gly Leu Gly Arg
 1               5


<210> SEQ ID NO 20
<211> LENGTH: 7
<212> TYPE: PRT
<213> ORGANISM: artificial sequence
<220> FEATURE:
<223> OTHER INFORMATION: synthetic polymer

<400> SEQUENCE: 20

Gly Ser Ile Gly Leu Gly Lys
 1               5


<210> SEQ ID NO 21
<211> LENGTH: 7
<212> TYPE: PRT
<213> ORGANISM: artificial sequence
<220> FEATURE:
<223> OTHER INFORMATION: synthetic polymer

<400> SEQUENCE: 21

Val Ser Ile Gly Leu Gly Lys
 1               5


<210> SEQ ID NO 22
<211> LENGTH: 7
<212> TYPE: PRT
<213> ORGANISM: artificial sequence
<220> FEATURE:
<223> OTHER INFORMATION: synthetic polymer

<400> SEQUENCE: 22

Gly Ser Asn Gly Leu Gly Lys
 1               5


<210> SEQ ID NO 23
<211> LENGTH: 7
<212> TYPE: PRT
```

-continued

<213> ORGANISM: artificial sequence
<220> FEATURE:
<223> OTHER INFORMATION: synthetic polymer

<400> SEQUENCE: 23

Gly Ser Ile Gly Leu Gly Ser
1 5

<210> SEQ ID NO 24
<211> LENGTH: 7
<212> TYPE: PRT
<213> ORGANISM: artificial sequence
<220> FEATURE:
<223> OTHER INFORMATION: synthetic polymer

<400> SEQUENCE: 24

Gly Ser Ile Gly Leu Gly Arg
1 5

<210> SEQ ID NO 25
<211> LENGTH: 38
<212> TYPE: DNA
<213> ORGANISM: artificial sequence
<220> FEATURE:
<223> OTHER INFORMATION: synthetic polymer

<400> SEQUENCE: 25
cgctggagcg gctgttgtca gcataggcct tgggaagg 38

<210> SEQ ID NO 26
<211> LENGTH: 38
<212> TYPE: DNA
<213> ORGANISM: artificial sequence
<220> FEATURE:
<223> OTHER INFORMATION: synthetic polymer

<400> SEQUENCE: 26
ccttcccaag gcctatgctg acaacagccg ctccagcg 38

<210> SEQ ID NO 27
<211> LENGTH: 34
<212> TYPE: DNA
<213> ORGANISM: artificial sequence
<220> FEATURE:
<223> OTHER INFORMATION: synthetic polymer

<400> SEQUENCE: 27
gcggctgttg gcagcaacgg ccttgggaag gtgc 34

<210> SEQ ID NO 28
<211> LENGTH: 34
<212> TYPE: DNA
<213> ORGANISM: artificial sequence
<220> FEATURE:
<223> OTHER INFORMATION: synthetic polymer

<400> SEQUENCE: 28
gcaccttccc aaggccgttg ctgccaacag ccgc 34

<210> SEQ ID NO 29
<211> LENGTH: 39
<212> TYPE: DNA
<213> ORGANISM: artificial sequence
<220> FEATURE:
<223> OTHER INFORMATION: synthetic polymer

<400> SEQUENCE: 29

-continued gcagcatagg ccttgggagt gtgcttgtgg atattttgg 39

<210> SEQ ID NO 30
<211> LENGTH: 39
<212> TYPE: DNA
<213> ORGANISM: artificial sequence
<220> FEATURE:
<223> OTHER INFORMATION: synthetic polymer

<400> SEQUENCE: 30
ccaaaatatc cacaagcaca ctcccaaggc ctatgctgc 39

<210> SEQ ID NO 31
<211> LENGTH: 39
<212> TYPE: DNA
<213> ORGANISM: artificial sequence
<220> FEATURE:
<223> OTHER INFORMATION: synthetic polymer

<400> SEQUENCE: 31
gcagcatagg ccttgggagg gtgcttgtgg atattttgg 39

<210> SEQ ID NO 32
<211> LENGTH: 39
<212> TYPE: DNA
<213> ORGANISM: artificial sequence
<220> FEATURE:
<223> OTHER INFORMATION: synthetic polymer

<400> SEQUENCE: 32
ccaaaatatc cacaagcacc ctcccaaggc ctatgctgc 39

<210> SEQ ID NO 33
<211> LENGTH: 35
<212> TYPE: DNA
<213> ORGANISM: artificial sequence
<220> FEATURE:
<223> OTHER INFORMATION: synthetic polymer

<400> SEQUENCE: 33
gtcattgtgg gcaggatcat cttgtccgga aagcc 35

<210> SEQ ID NO 34
<211> LENGTH: 46
<212> TYPE: DNA
<213> ORGANISM: artificial sequence
<220> FEATURE:
<223> OTHER INFORMATION: synthetic polymer

<400> SEQUENCE: 34
gtgacccaac caggtatatt gattgagccc gaccaggaat gtgacc 46

<210> SEQ ID NO 35
<211> LENGTH: 30
<212> TYPE: DNA
<213> ORGANISM: artificial sequence
<220> FEATURE:
<223> OTHER INFORMATION: synthetic polymer

<400> SEQUENCE: 35
cagccatggc ctcacacctc ccttacatcg 30

<210> SEQ ID NO 36
<211> LENGTH: 33
<212> TYPE: DNA

-continued

<213> ORGANISM: artificial sequence
<220> FEATURE:
<223> OTHER INFORMATION: synthetic polymer

<400> SEQUENCE: 36
catgccatgg cgcatggcgt ggagcagtcc tcg 33

<210> SEQ ID NO 37
<211> LENGTH: 77
<212> TYPE: DNA
<213> ORGANISM: artificial sequence
<220> FEATURE:
<223> OTHER INFORMATION: synthetic polymer

<400> SEQUENCE: 37
ggggacaagt ttgtacaaaa aagcaggctt cgaaaacctg tattttcagg gcgcctcaca 60
cctcccttac atcgaac 77

<210> SEQ ID NO 38
<211> LENGTH: 54
<212> TYPE: DNA
<213> ORGANISM: artificial sequence
<220> FEATURE:
<223> OTHER INFORMATION: synthetic polymer

<400> SEQUENCE: 38
ggggaccact ttgtacaaga aagctgggtt tagcatggcg tggagcagtc ctcg 54

<210> SEQ ID NO 39
<211> LENGTH: 50
<212> TYPE: DNA
<213> ORGANISM: artificial sequence
<220> FEATURE:
<223> OTHER INFORMATION: synthetic polymer

<400> SEQUENCE: 39
agagcgtctt tacaggcctc acccacatag acgcccattt cttgtcccag 50

<210> SEQ ID NO 40
<211> LENGTH: 49
<212> TYPE: DNA
<213> ORGANISM: artificial sequence
<220> FEATURE:
<223> OTHER INFORMATION: synthetic polymer

<400> SEQUENCE: 40
agggcgccag gggagaggat agcagggagt aggttaacca ggtcctcgg 49

<210> SEQ ID NO 41
<220> FEATURE:
<223> OTHER INFORMATION: Synthetic

<400> SEQUENCE: 41

000

<210> SEQ ID NO 42
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 2, 7
<223> OTHER INFORMATION: Xaa = Any Amino Acid -continued

```
<400> SEQUENCE: 42

Gly Xaa Ile Gly Leu Gly Xaa
 1               5
```

METHODS AND COMPOSITIONS FOR IDENTIFYING ANTI-HCV AGENTS

FIELD OF THE INVENTION

The invention relates to methods and compositions for identifying agents for the treatment of HCV infection.

BACKGROUND OF THE INVENTION

Hepatitis C virus (HCV) is an example of a Flaviviridae virus and is the principal etiological agent of post-transfusion and community-acquired non-A non-B hepatitis worldwide. It is estimated that over 150 million people worldwide are infected by the virus. A high percentage of carriers become chronically infected with this pathogen and many patients progress to a state of chronic liver disease, so-called chronic hepatitis C. This group is in turn at high risk for serious liver disease such as liver cirrhosis, hepatocellular carcinoma and terminal liver disease leading to death.

HCV is an enveloped positive strand RNA virus. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce structural and non-structural (NS) proteins. In the case of HCV, the generation of mature nonstructural proteins (NS2, NS3, NS4A, NS4B, NS5A, and NS5B) is effected by two viral proteases. The first one is a metalloprotease located in NS2 that cleaves the NS2-NS3 junction in cis; the second one is a serine protease contained within the N-terminal region of NS3 (henceforth referred to as NS3 protease) and mediates all the subsequent cleavages downstream of NS3, both in cis, at the NS3-NS4A cleavage site, and in trans, at the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components.

The mechanism by which HCV establishes viral persistence and causes a high rate of chronic liver disease has not been elucidated. Antiviral interventions to date have focused upon, for example, ribavirin and interferon-alpha (IFN-$\alpha$)-based monotherapy and combination therapy. However, not all patients are responsive to these therapies.

As such, a great need exists for identifying anti-HCV agents, and methods for combating HCV infections. The described invention meets this, and other, needs.

Literature

Literature of interest includes: Hugle et al, 2001 Virology 284:70-81; Gorbalenya and Koonin 1989 Nucleic Acids Res 17:8413-8440; Bartenschlager and Lohmann 2000 Virology 81 Pt 7:1631-1648; Reed and Rice 2000 Current Topics in Microbiology and Immunology 242:55-84; Mirzayan and Wimmer 1992 Virology 189:547-555; Rodriguez and Carrasco 1993 J. Biol Chem 268:8105-8110; and Piccininni 2002 J. Biol Chem 277:45670-45679; and published patent applications US20030087873, US20020147160 and WO99/01582.

SUMMARY OF THE INVENTION

The invention provides methods and compositions for identifying agents for treating infection by viruses that encode a nucleotide-binding NS4B protein, or functional equivalent thereof, e.g., hepatitis C virus (HCV) or other members of the family Flaviviridae. In general, the methods involve contacting an NS4B nucleotide binding motif (NBM)-containing polypeptide with a candidate agent, and determining the effect of the candidate agent on nucleotide binding activity, a nucleotide hydrolyzing activity, or a nucleotide-dependent RNA binding activity of the polypeptide. A candidate agent that inhibits NS4B polypeptide binding to a nucleotide is an anti-viral agent, e.g., an anti-HCV agent. The invention also features a polynucleotide encoding a NS4B polypeptide having a modified NBM (e.g., which is impaired in NTP binding). The subject methods and compositions find use in a variety of therapeutic and screening applications.

BRIEF DESCRIPTION OF THE DRAWINGS

FIGS. 1A-1C show conserved sequence elements in nucleotide binding motif (NBM)-containing proteins. One conserved element of the NBM is the so-called "A-motif." Other conserved elements that may participate in nucleotide binding ("G," "PM2" "B-motif") are also indicated. Consensus sequences of the NBM from: (1A) some representative family members of the G-protein superfamily of GTP-binding proteins; (1B) selected viruses with the indicated NBM-containing protein. (1C) A NBM was located in HCV NS4B. The amino acid sequence of the consensus for all HCV isolates available for examination, the genotype 1b clone used, genotype 3, and the engineered NS4B mutants G129V, I131N, K135S and K135R are indicated. X=any amino acid. GXGGVGKS: SEQ ID NO: 1; GDGAXGKT: SEQ ID NO: 2; GLDAAGKT: SEQ ID NO: 3; GHVDHGKT: SEQ ID NO: 4; DTAG: SEQ ID NO: 5; DVGG: SEQ ID NO: 6; DCPG: SEQ ID NO: 7; GPGGSGKS: SEQ ID NO: 8; GKRGGGKS: SEQ ID NO: 9; GSPGTGKS: SEQ ID NO: 10; GPASTGKT: SEQ ID NO: 11; GKSRTGKS: SEQ ID NO: 12; GAPGIGKT: SEQ ID NO: 13; GSIGLGK: SEQ ID NO: 14; GSIGLGR: SEQ ID NO: 15; VSIGLGK: SEQ ID NO: 16; GSNGLGK: SEQ ID NO: 17; GSIGLGS: SEQ ID NO: 18; GSIGLGR: SEQ ID NO: 19.

FIGS. 3A, 3B and 3C are each composed of an autoradiograph (top), a western blot analysis with an anti-GFP antibody (middle) and a graph quantifing nucleotide binding relative to wild type control (bottom). (3A) Binding of labeled GTP is progressively decreased in the presence of increasing concentrations of cold competitor nucleotide. Huh-7 cells were transfected with a plasmid encoding NS4B-GFP. Membrane preparations were incubated with 10 μM labeled GTP compound in the absence (lane 1) or presence of 1 mM (lane 2) or 100 μM (lane 3) competing cold GTPγS, followed by immunoprecipitation as in FIG. 2A above. (3B) NS4B-GFP binds ATP significantly less efficiently than GTP. Membrane preparations prepared from Huh-7 cells transfected with plasmids encoding NS4B-GFP (lanes 4 and 5) or GFP (lanes 6 and 7) were incubated with equal concentrations of labeled ATP (lanes 4 and 6) or GTP (lanes 5 and 7), followed by immunoprecipitation as in FIG. 2A. (3C) Mutations within the NBM impair GTP binding. Huh-7 cells were transfected with plasmids encoding wild type NS4B-GFP (lane 8) or NS4B-GFP with one of the following NBM mutations: Ile131Asn mutation ("IN") (lane 9), Gly129Val mutation ("GV") (lane 10), Lys135Ser mutation ("KS") (lane 11) or Lys135Arg ("KR") (lane 12). As above, membrane fractions were incubated with labeled GTP followed by immunoprecipitation. Experiments were repeated between two to four times. When present, any detectable binding of GTP to the 5A-GFP negative control protein was used for background subtraction purposes. Representative gels are shown. Mean values are plotted in the graphs and error bars represent SE.

Figure 4:
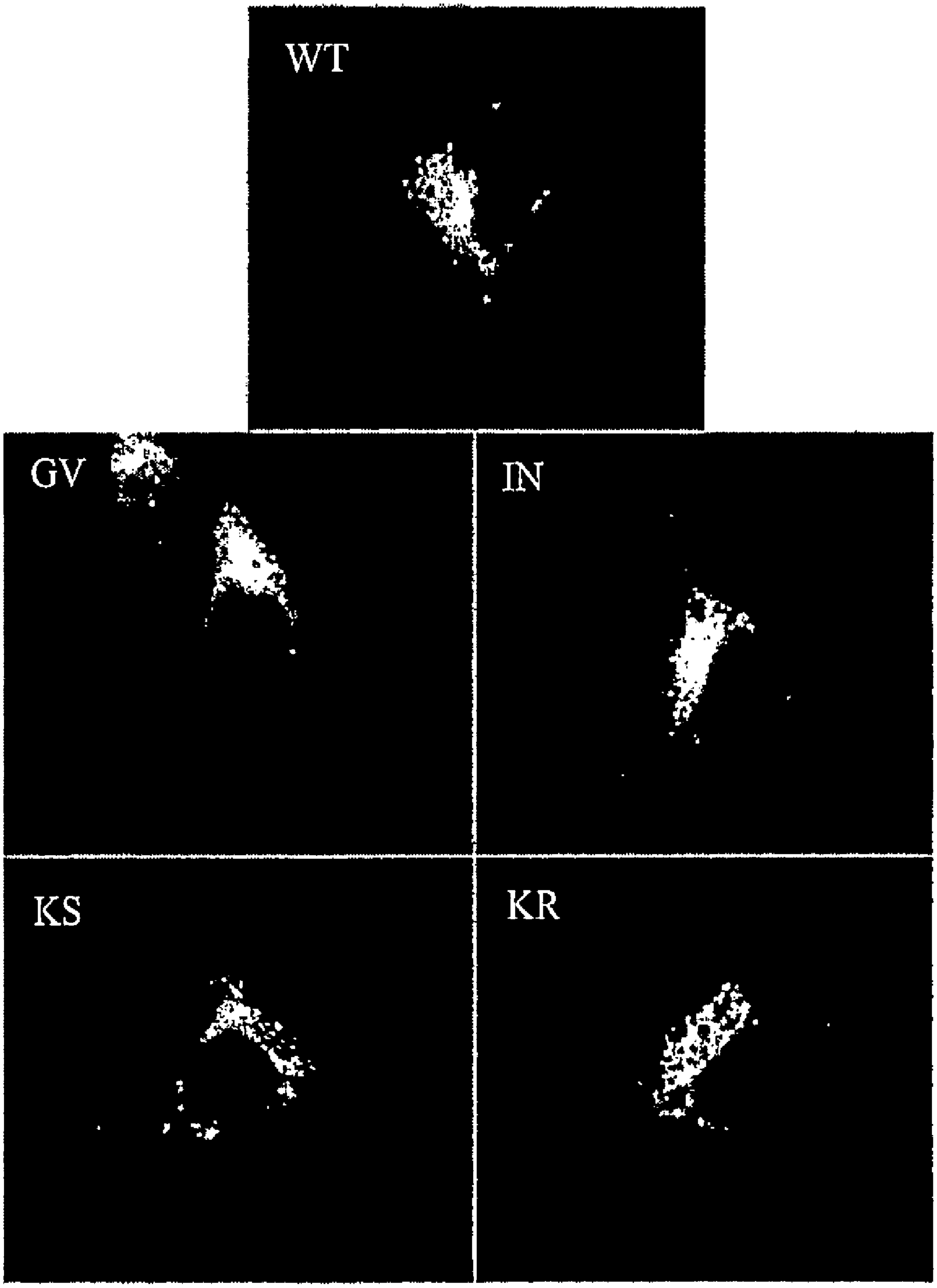

FIG. 4 is five panels of fluorescence images showing that mutations within NS4B's NBM are not associated with obvious changes in protein expression level or intracellular distribution pattern. Huh-7 cells plated on coverslips were transfected with plasmids encoding wild type NS4B-GFP (upper panel), or NS4B-GFP with one of the following NBM mutations: Gly129Val mutation ("GV") (left middle panel), Ile131Asn mutation ("IN") (right middle panel), Lys135Ser mutation ("KS") (left lower panel) or Lys135Arg ("KR") (right lower panel). Eighteen hours post transfection the cells were fixed and imaged by fluorescence microscope. Note that all of these proteins display the same reticular membrane localization pattern with distinct foci located in the cytoplasm that is characteristic of wild type NS4B.

Figure 5A:
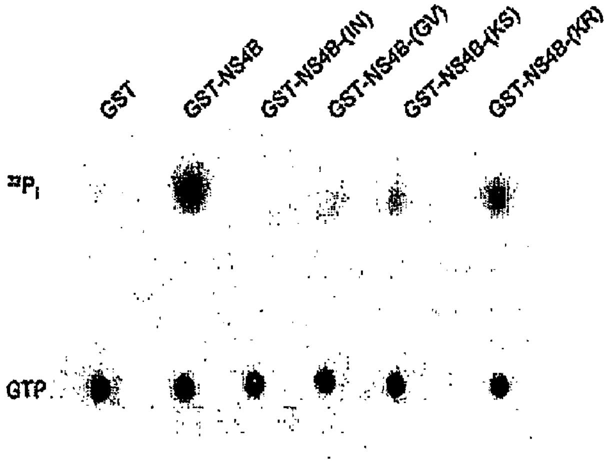
Figure 5B:
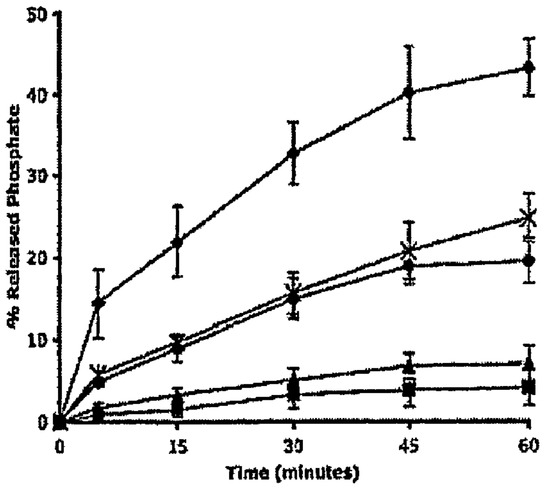

FIGS. 5A and 5B show that NS4B has GTPase activity which is mediated by an NBM. Equal amounts of purified GST, GST-NS4B, and the NBM mutants GST-NS4B(GV), GST-NS4B(IN), GST-NS4B(KS), and GST-NS4B(KR) were incubated with [$\gamma^{32}$P]GTP. Aliquots were collected every 15 minutes and subjected to thin-layer chromatography (TLC) to allow separation of hydrolyzed $^{32}$Pi from GTP followed by autoradiography and phosphorimager analysis. (5A) A representative TLC plate. Locations of GTP and $^{32}$Pi standards are indicated on the left. (5B) GTPase activity of wild type NS4B (υ), GV (σ), IN (ν), KS (λ) and KR (5) mutants is plotted as a function of time. When present, any detectable hydrolysis of GTP in the GST control was used for background subtraction purposes. Each data point represents the average of at least four independent determinations. The error bars represent standard deviation.

FIGS. 6A and 6B show engineered mutations in NS4B's nucleotide binding motif (NBM). (6A) The consensus sequence for all NBM-containing proteins, all HCV isolates, and HCV genotype 1b are indicated. X is any amino acid. (6B) Single amino acid point mutations (shaded in gray) were engineered into the NBM of NS4B at the indicated codon positions. GSIGLGK: SEQ ID NO: 20; VSIGLGK: SEQ ID NO: 21; GSNGLGK: SEQ ID NO: 22; GSIGLGS: SEQ ID NO: 23; GSIGLGR: SEQ ID NO: 24.

Figure 7A:
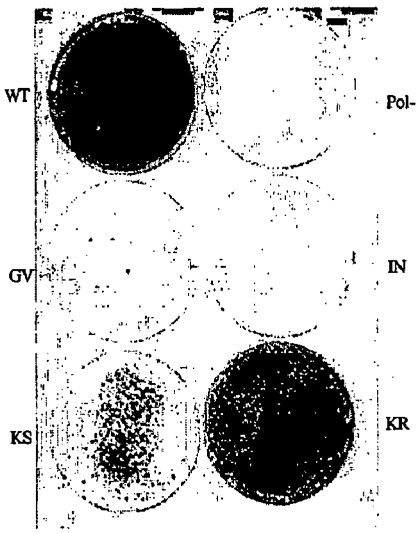
Figure 7B:
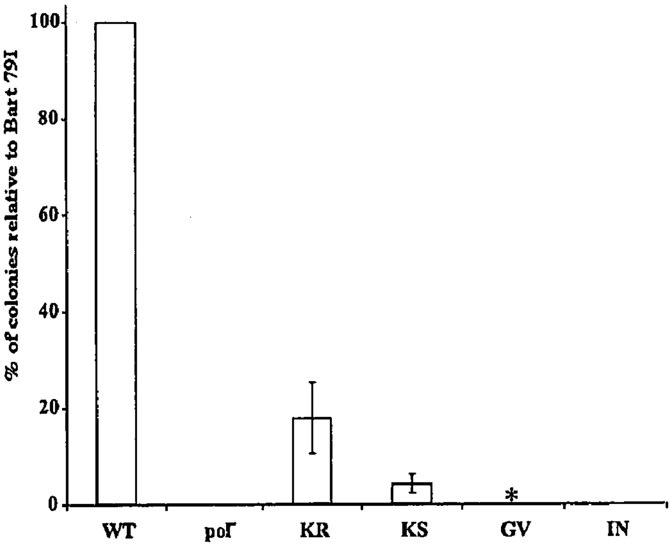

FIGS. 7A and 7B show that genetic disruption of NS4B's NBM impairs HCV RNA replication. Replication of HCV replicons harboring the mutations depicted in FIG. 5B were assayed by colony formation assays. (7A) Wild type and mutant replicons were electroporated into Huh-7 cells and G418-resistant colonies were selected and stained with crystal violet. These replicons contain the gene for neomycin-phosphotransferase. Each dot represents a colony of Huh-7 cells that was able to grow in the presence of G418 due to the presence of efficiently replicating intracellular replicons. WT=Bart79I (wild type) (6, 3); pol—=Bart79I with a lethal mutation in NS5B (16); KR=Bart79I with a Lys135Arg point mutation; KS=Bart79I with a Lys135Ser point mutation; GV=Bart79I with a Gly129Val point mutation; IN=Bart79I with an Ile131Asn point mutation. A representative plate is shown. (7B) The percentage of colonies relative to wild type control is plotted. Note rare colonies were obtained with the GV mutant (*) and none with the pol— or IN mutants.

Figure 8:
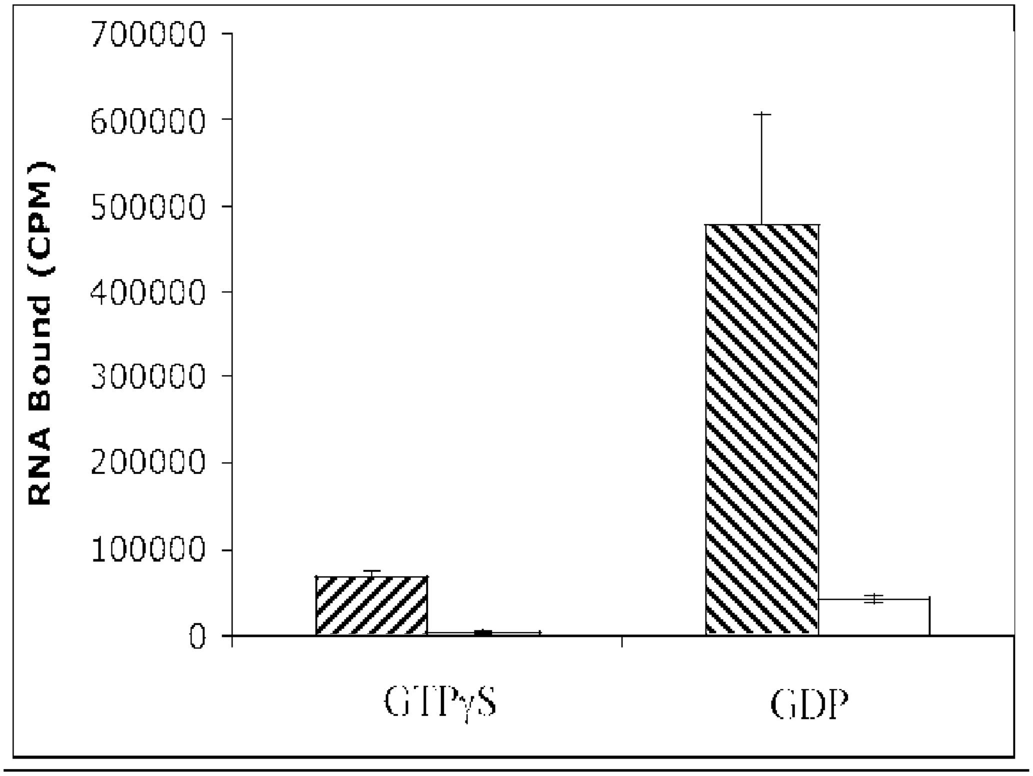

FIG. 8 is a graph showing that NS4B binds HCV RNA and binding is regulated by guanyl nucleotides. Equal amounts of purified GST or GST-NS4B were incubated with $^{32}$P-labeled in vitro transcribed HCV RNA in the presence of GDP or GTP-γ-S followed by binding to glutathione beads and washes. RNA binding activity of GST-NS4B (hatched bars) and GST (white bars), as measured by liquid scintillation counting of sample aliquots, is plotted. Each data point represents the average of at least six independent determinations. The error bars represent standard deviation.

Figure 9:
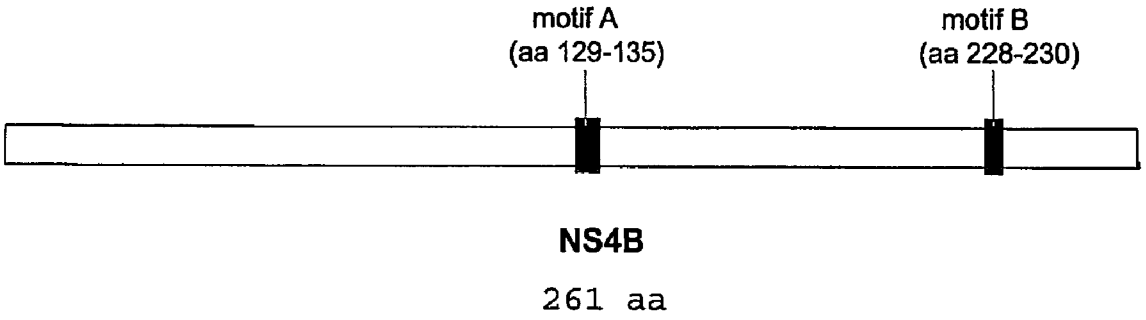

FIG. 9 is a schematic representation of an HCV NS4B protein showing NBM motifs A and B.

DEFINITIONS

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The disclosure of U.S. provisional application Ser. No. 60/497,124, filed Aug. 22, 2003, is incorporated herein in its entirety for all purposes.

It must be noted that as used herein and in the appended claims, the singular forms "a", "and", and "the" include plural referents unless the context clearly dictates otherwise. Thus, for example, reference to "an NS4B polypeptide" includes a plurality of such polypeptides and reference to "the NS4B nucleotide binding motif" includes reference to one or more NS4B nucleotide binding motif and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A "nucleotide binding motif" or "NBM" as used herein refers to a region of a viral NS4B polypeptide that binds a nucleotide triphosphate (NTP), which NTP can be GTP, ATP, TTP, or CTP, and usually is at least GTP.

A "nucleotide binding NS4B protein" or "NS4B protein" is any viral NS4B protein, or functional equivalent thereof (e.g., proteins that are encoded by other viruses by are equivalent to NS4B, but not named NS4B), that contains a nucleotide binding motif, binds a nucleotide, and binds RNA in the presence of a nucleotide. NS4B proteins are typically characterized by an N-terminal amphipathic helix, at least two transmembrane domains, and an NBM, where the NBM facilitates nucleotide binding. NS4B proteins may be identified using a number of methods, e.g., by pairwise sequence alignment between the HCV NS4B protein and the proteins encoded by other viruses. Such proteins may be encoded by any virus type, particularly those viruses of the Flaviviridae family. The NS4B polypeptide may also itself be contained within a larger polypeptide such as one encoding a replication-competent form of a viral polyprotein.

By "Flaviviridae virus" is meant any virus from the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355,D11168,AJ238800,NC_001809,NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

A "variant" of a polypeptide (e.g., an NS4B polypeptide or a NS4B nucleotide binding motif of a polypeptide) is defined as a polypeptide that is altered by one or more amino acid residues. Such alterations include amino acid substitutions, deletions or insertions, or a combination thereof. Variants of NS4B, particularly those that have conservative amino acid substitutions, usually retain their basic structural features and biological activity in viral replication. Variants of an NS4B nucleotide binding motif may retain a nucleotide binding activity, and allow HCV virus replication. NS4B variants may alternatively have decreased nucleotide binding activity (e.g., a decreased binding affinity or avidity relative to a wildtype NS4B of, for example, the same viral origin), may have constitutive nucleotide binding activity, or may have enhanced nucleotide binding activity (e.g., an increased binding affinity or avidity relative to a wildtype NS4B of, for example, the same viral origin). Such variants are useful in the production of, for example, attenuated viral vaccines.

Guidance in determining which and how many amino acid residues may be substituted, inserted or deleted (e.g., without abolishing activity) may be found by comparing the sequence of a polypeptide to the sequence of a polypeptide with a related structure and function e.g., between sequences from HCV strains or genotypes. Assays for HCV are readily available and straightforward, and can be readily applied to determine which and how many amino acid residues may be substituted, inserted or deleted may be determined empirically.

A "substitution" results from the replacement of one or more amino acids or nucleotides by different amino acids or nucleotides, respectively as compared to an amino acid sequence or nucleotide sequence of a polypeptide. If a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: gly, ala; val, ile, leu; asp, glu; asn, gln; ser, thr; lys, arg; and phe, tyr. It is understood that NS4B NBM polypeptides may have conservative amino acid substitutions which have substantially no effect on HCV viral replication. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide or polynucleotide sequence, a deletion can involve deletion of about 2, about 5, about 10, up to about 20, up to about 30 or up to about 50 or more amino acids. A NS4B NBM polypeptide may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition to one or more amino acid residues within an amino acid sequence of a polypeptide, while "addition" can be an insertion or refer to amino acid residues added at the N- or C-termini. In the context of a polypeptide or polynucleotide sequence, an insertion or addition may be of up to about 10, up to about 20, up to about 30 or up to about 50 or more amino acids. A NS4B NBM polypeptide may contain more than one insertion.

A "biologically active" NS4B polypeptide refers to a polypeptide having structural and biochemical functions of a naturally occurring NS4B protein.

"Non-native", "non-endogenous", and "heterologous", in the context of a polypeptide, are used interchangeably herein to refer to a polypeptide having an amino acid sequence or, in the context of an expression system or a viral particle, present in an environment different to that found in nature.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Operably linked" refers to an arrangement of elements wherein the components so described are configured so as to perform their usual function. Thus, a given polypeptide that is operably linked to a HCV NS4B nucleotide binding motif binds nucleotides. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., infra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

A first polynucleotide is "derived from" a second polynucleotide if it has the same or substantially the same nucleotide sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

The term "unit dosage form" as used herein refers to physically discrete units suitable as unitary dosages for subjects (e.g., animals, usually humans), each unit containing a predetermined quantity of an agent, e.g. a plasmid in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of modified NS4B polypeptide-encoding nucleic acids that can provide for enhanced or desirable effects in the subject (e.g., reduction of pathogen load, increase in CD4 count, reduction of disease symptoms, etc.).

"Subject", "host" and "patient" are used interchangeably herein, to refer to an animal, human or non-human, susceptible to or having an infection by an intracellular pathogen and amenable to therapy according to the methods of the invention. Generally, the subject is a mammalian subject. Exemplary subjects include, but are not necessarily limited to, humans, cattle, sheep, goats, pigs, dogs, cats, and horses, with humans being of particular interest.

DETAILED DESCRIPTION OF THE INVENTION

The invention provides methods and compositions for identifying agents for treating infection by viruses that encode a nucleotide-binding NS4B protein, or functional equivalent thereof, e.g., hepatitis C virus (HCV) or other members of the family Flaviviridae. In general, the methods involve contacting an NS4B nucleotide binding motif (NBM)-containing polypeptide with a candidate agent, and determining the effect of the candidate agent on nucleotide binding activity, a nucleotide hydrolyzing activity, or a nucleotide-dependent RNA binding activity of the polypeptide. A candidate agent that inhibits NS4B polypeptide binding to a nucleotide is an anti-viral agent, e.g., an anti-HCV agent. The invention also features a polynucleotide encoding a NS4B polypeptide having a modified NBM (e.g., which is impaired in NTP binding). The subject methods and compositions find use in a variety of therapeutic and screening applications.

The invention is based on the discovery that the HCV NS4B polypeptide contains a nucleotide binding motif (NBM), can hydrolyze nucleotides, and can bind RNA in the presence of nucleotide. Accordingly, the NBM can serve as a target for antiviral therapy. In addition, because other viruses, e.g., viruses of the family Flaviviridae etc., also have NS4B polypeptides containing a NBM, the invention also encompasses identification of antiviral agents that inhibit replication by other viruses.

In one embodiment, the invention provides methods and compositions for identifying agents for inhibiting viral replication by an NS4B-encoding virus, with HCV and Flaviviridae viruses being of particular interest. Such antiviral compositions can be applied to the treatment of virus infection (e.g., to inhibit replication, reduce viral load, and the like). In general, the methods for identifying an antiviral agent involve contacting a polypeptide having an NS4B nucleotide binding motif with a candidate agent, and determining the effect of the candidate agent on a nucleotide binding activity, a nucleotide hydrolyzing activity, or a nucleotide-dependent RNA binding activity of the polypeptide. A candidate agent that inhibits any of these activities is an anti-viral agent.

The invention further provides an NS4B polypeptide having a modified nucleotide binding motif, e.g., a nucleotide binding motif that is impaired in nucleotide binding, and a polynucleotide encoding this polypeptide. The invention also provides modified viral genomes encoding a modified NBM.

Also provided by the subject invention are methods of inhibiting cellular replication of any virus encoding an NS4B protein, or functional equivalent thereof, that contains a nucleotide binding domain. For example, Flaviviridae virus, particularly HCV, replication may be inhibited using the subject methods. The invention also features kits for use in the subject methods are provided. The subject methods and compositions find use in a variety of therapeutic and screening applications.

NS4B encoding viruses include Flaviviridae family viruses, include, but are not limited to flaviviruses, pestiviruses and hepatitis C viruses that include, yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Hepatitis C virus; Kunjin virus; Central European encephalitis virus; Russian spring-summer encephalitis virus; Powassan virus; Kyasanur Forest disease virus; and Omsk hemorrhagic fever virus. HCV is of particular interest in the invention.

Identification of anti-HCV agents according to the invention, and their use in inhibiting HCV replication and treating HCV infection, is of particular interest. The HCV contemplated by the invention may be of any genotype (genotype 1, 2, 3, 4, 5, 6, and the like), as well as subtypes of an HCV genotype (e.g., 1a, 1b, 2a, 2b, 3a, etc.)). Because currently HCV genotype 1 is normally the most difficult to treat, HCV genotype 1 and genotype 1 subtypes are of particular interest.

While the specification below refers to HCV, such is only for clarity and is not intended to limit the invention as described in more detail below to HCV. As noted above, the invention can be applied to any virus encoding a nucleotide-binding NS4B protein, e.g., a Flavivirdae virus having an NS4B polypeptide that contains an NBM.

In further describing the invention in greater detail than provided in the Summary and as informed by the Background and Definitions provided above, the compositions for use in the subject methods are described first, followed by a discussion of methods for screening for anti-HCV agents. This discussion is followed by a description of methods of inhibiting HCV in a cell, a review of representative applications in which the subject methods find use, and subject kits provided for practicing the subject methods.

NS4B NBM Polypeptides

An "NS4B NBM polypeptide" is any polypeptide that has nucleotide binding activity and contains a NS4B NBM. In other words, an NS4B NBM polypeptide is any polypeptide that contains a NBM from a viral NS4B protein, i.e., proteins that are functional equivalent of the NS4B of HCV (e.g., in another virus, e.g., in a virus of the Flaviviridae virus family (e.g., HCV, BVDV, and the like), a fusion protein containing an NBM-containing fragment of a NS4B polypeptide operably linked to a fusion partner, a naturally-occurring NS4B protein, or the like. Such polypeptides find use in, for example, screening assays for anti-viral agents.

In many embodiments, NS4B NBM polypeptides contain an NS4B NBM, where an "NS4B NBM" has a sequence conforming to a NS4B NBM consensus sequence: G-S/G-I/V-G-L/I-G-K/R or, in other embodiments G-S/G-I-G-L-G-K/R, examples of which may be found in any naturally occurring HCV NS4B polypeptide, e.g., those shown in the FIG. 1. NS4B NBM polypeptides therefore contain at least 7 amino acids conforming to the NS4B NBM consensus sequence, which 7 amino acids may be contained within a larger polypeptide, such as a polypeptide of 20 or more amino acids, 50 or more amino acids, 100 or more amino acids, 200 or more amino acids, 400 or more amino acids or 600 amino acids or more, usually up to about 1000 amino acids or more. NS4B NBM polypeptides may contain a fragment of 10 or more amino acids, 20 or more amino acids, 50 or more amino acids, 100 or more amino acids, 200 or more amino acids, sometimes up to about 300 amino acids of a naturally occurring HCV NS4B polypeptide.

In certain embodiments the fusion partner may be a reporter protein, e.g., a light emitting reporter such as a fluorescent or luminescent polypeptide (for example GFP or luciferase), may contain sequences from another nucleotide-binding polypeptide (e.g., a G-protein), or may contain sequence from any other polypeptide. In certain embodiments, the NBM-containing fragment of an HCV NS4B polypeptide may also contain other motifs associated with nucleotide-binding, including "G", "PM" "D" motifs, as shown in FIG. 1. In these embodiments, these motifs have the amino acids sequences "F", "T" and "DAAA" (SEQ ID NO:41), respectively. In other embodiments, however, an NS4B NBM polypeptide may be a naturally-occurring NS4B protein or a variant thereof, or in other embodiments, a non-naturally occurring NS4B protein. FIG. 9 shows the position of the GTP binding domains of HCV NS4B. In particular embodiments, an NS4B NBM polypeptide is a fusion protein between an NS4B NBM and a partner such as GST , poly-histidine, or avidin. These fusions are convenient for assay formats using glutathione, nickel, or biotin coupled to solid supports (using beads or a microtiter plate well, etc.).

Variant NS4B NBM polypeptides that retain nucleotide-binding activity usually have a sequence conforming to the NS4B NBM consensus sequence: G-S/G-I/V-G-L/I-G-K/R or, in other embodiments G-S/G-I-G-L-G-K/R (SEQ ID NO:42), as discussed above, and in addition, may have G, PM2 and B motifs, spaced from the consensus sequence at an appropriate distance, as discussed in Dever et al., (Proc Natl Acad Sci U S A. 1987 84:1814-8) although their precise spacing distance is not as important as their relationship to each other in the polypeptide tertiary structure.

Variant NS4B NBM polypeptides that have reduced (including abolished) NTP-binding activity, as compared to a naturally occurring NS4B NBM, are generally altered in the NBM, and/or the G, PM2 or P motifs such that they can no longer bind or have nucleosidase activity (e.g., the ability to hydrolyse a nucleotide). In many embodiments variant NS4B NBM polypeptides that have reduced nucleotide-binding activity have the sequence "$X_1X_2X_3X_4X_5X_6X_7$", where $X_1$ is an amino acid other than Gly, $X_2$ is an amino acid other than Ser or Gly, $X_3$ is an amino acid other then Ile or Val, $X_4$ is an amino acid other than Gly, $X_5$ is an amino acid other than Leu or Ile, $X_6$ is an amino acid other than Gly and $X_7$ is an amino acid other than Lys or Arg, or in other embodiments, they have the sequence $X_1X_2X_3X_4X_5X_6X_7$, where $X_1$ is an amino acid other than Gly, $X_2$ is an amino acid other than Ser or Gly, $X_3$ is an amino acid other then Ile, $X_4$ is an amino acid other than Gly, $X_5$ is an amino acid other than Leu, $X_6$ is an amino acid other than Gly and $X_7$ is an amino acid other than Lys or Arg. In general, any amino acid other than Phe or Tyr in the G motif, any amino acid other than T at the PM2 motif, and any amino acid other than Asp or Gly at the first position of the B motif, will reduce the GTP binding activity of a NS4B NBM polypeptide. NSB4 NBM polypeptides having reduced GTP-binding are useful as controls in screening assays, and find use in research application in investigating the role of NS4B in viral replication.

It is envisioned that mutations in positions $X_3$ or $X_4$ within the A motif of a NS4B NBM confer constitutive constitutively active to NS4B, in the same manner as equivalent mutations in the ras protein. For example, substitution of either Gly in position $X_3$ with Val (Ras G12V) or Gly in position $X_4$ with Asp (Ras G13D) results in mutants with oncogenic potential (Valencia, A. et al. Biochemistry, 30 (19):4637-4648, 1991). Similarly, mutation of the $X_8$ position can lead to a dominant negative Ras mutant, such as the Ras S17N dominant negative mutant (Feig, L. A. et al. Molecular & Cellular Biology, 8(8):3235-43, 1988). Similar variations of NS4B NBM are included in the present invention. These include constitutively active and dominant negative modified versions of an NS4B NBM, such as those made by altering the amino acids at the $X_3$, $X_4$, or $X_8$ positions (e.g., to Val, Asp and Asn), respectively.

Nucleic Acids Encoding NS4B NBM Polypeptides

Since the genetic code and recombinant techniques for manipulating nucleic acid are known, and the amino acid sequences of NS4B NBM polypeptides are described above, the design and production of nucleic acids encoding a NS4B NBM polypeptide is well within the skill of an artisan. In certain embodiments, standard recombinant DNA technology (Ausubel, et al, *Short Protocols in Molecular Biology,* 3rd ed., Wiley & Sons, 1995; Sambrook, et al., *Molecular Cloning: A Laboratory Manual*, Second Edition, (1989) Cold Spring Harbor, N.Y.) methods are used. For example, naturally occurring NS4B NBM polypeptide coding sequences may be isolated from a library of nucleic acids using any one or a combination of a variety of recombinant methods that do not need to be described herein. Subsequent substitution, deletion, and/or addition of nucleotides in the nucleic acid sequence encoding a protein may also be done use standard recombinant DNA techniques.

For example, site directed mutagenesis and subcloning may be used to introduce/delete/substitute nucleic acid residues in a polynucleotide encoding a NS4B NBM polypeptide. In other embodiments, PCR may be used. Nucleic acids encoding a NS4B NBM polypeptide may also be made by chemical synthesis entirely from oligonucleotides (e.g., Cello et al., Science (2002) 297:1016-8).

In certain embodiments, the codons of the nucleic acids encoding an NS4B NBM polypeptide are optimized for expression in cells of a particular species, particularly a mammalian, e.g., human or mouse, species.

The invention further provides vectors (also referred to as "constructs") comprising a subject nucleic acid. In many embodiments of the invention, the subject nucleic acid sequences may be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology,* 3rd ed., Wiley & Sons, 1995; Sambrook, et al., *Molecular Cloning: A Laboratory Manual,* Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used. In certain embodiments, however, the subject nucleic acids are contained the genome of HCV, where the genome has been genetically modified such that it contains a non-naturally occurring NS4B polypeptide-encoding sequence.

A variety of expression vectors are available to those in the art for purposes of producing a polypeptide of interest in a cell. One suitable vector is pCMV, which used in certain embodiments. This vector is publicly available from the American Type Culture Collection (ATCC) and was deposited on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The subject nucleic acids usually contain an single open reading frame encoding a subject NS4B NBM polypeptide, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (ISA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, NS4B NBM polypeptides may be fusion proteins. Methods for making fusions between to or more nucleic acids encoding a fusion protein, are well within the skill of one of skill in the art and will not be described any further.

The subject nucleic acids may also contain restriction sites, multiple cloning sites, primer binding sites, ligatable ends, recombination sites etc., usually in order to facilitate the construction of a nucleic acid encoding a polypeptide of interest.

In certain embodiments, a subject nucleic acid may be a modified viral (e.g., HCV) genome, or model thereof, that encodes an NS4B polypeptide having altered nucleotide binding activity, as described above. In these embodiments, the nucleic acid, either RNA or DNA, may be part of a virus particle. In certain embodiments, viral nucleic acids encoding a wild-type NS4B NBM are replaced by nucleic acids encoding an NS4B NBM with modified nucleotide binding activity.

Host Cells

The invention further provides host cells, including isolated in vitro host cells (e.g., for construct production and/or use in screening assays) and in vivo host cells of a non-human animal, that comprise a subject nucleic acid.

*E. coli* is a prokaryotic host useful for cloning the nucleic acid sequences of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* or *Picha* are preferred hosts, with suitable vectors having expression control sequences, such as promoters, including the 3-phosphoglycerate kinase promoter or those of other glycolytic enzyme genes, and an origin of replication, termination sequences and the like as desired.

In addition to microorganisms, mammalian tissue cell culture may also be used to express and produce the polypeptides of the present invention (see, Winnacker, “From Genes to Clones,” VCH Publishers, New York, N.Y. (1987). Suitable mammalian cells include CHO cell lines, various COS cell lines, HeLa cells, and myeloma cell lines, etc.

The subject modified polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher. organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Polypeptides can also be synthesized in the laboratory. Polypeptides that are subsets of the complete sequences of the subject proteins may be used to identify and investigate parts of the protein important for function.

In embodiments of particular interest, the host cell is a mammalian (e.g.) human cell that may be infected with HCV (including models thereof). In certain embodiments the human cell is a CHOP cell, a huh7 cell or a H9C2 cell, B-cell lines including B-cell lymphoma cells, and the cell is chosen because it is susceptible to infection by HCV or can support the replication of HCV or HCV replicons. The latter include a wide variety of cells (including but not limited to primary human, mouse, or rat liver cells, or cell lines originally derived from primary cells such as HeLa, Hepa-6, MDCK, etc.) where each cell type has its own set of preferred adaptive mutations.

In addition, the invention contemplates use of animal models of viral infection, particularly HCV infection.

Methods

The invention provides screening assays to identify anti-HCV agents, methods of modulating the activity of an HCV NS4B polypeptide and methods of inhibiting viral replication in a cell.

Screening Assays

The invention provides methods to identify anti-viral agents. In general, the methods involve contacting a NS4B NBM polypeptide with a candidate agent, and determining an effect of the candidate agent on a nucleotide binding activity, a nucleotide hydrolyzing activity, or a nucleotide-dependent RNA binding activity of the polypeptide. In many embodiments, a candidate agent that inhibits a nucleotide binding activity of the polypeptide is an anti-viral agent. What is meant by "inhibits a nucleotide binding activity" is reducing an activity related to nucleotide binding, such as, for example, the affinity of the polypeptide to a nucleotide, the specificity of the polypeptide to a nucleotide, or, in certain embodiments, a conformation change in the polypeptide that is induced by nucleotide binding or the ability of the polypeptide to catalyze a reaction of said nucleotide (e.g., hydrolysis, etc), where the nucleotide can be dGTP, dATP, dTTP or dCTP, including analogs and/or variants thereof, including ribonucleotides, etc., and polymers thereof.

In general, an anti-HCV agents identified using the subject screening assay will inhibit an activity (i.e., a nucleotide binding activity, a nucleotide hydrolyzing activity, or a nucleotide-dependent RNA binding activity) of a NS4B NBM polypeptide by more than about 20%, more than about 40%, more than about 60%, more than about 80%, more than about 90%, or more than about 95%, or more than about 98%, usually up to about 100%, as compared to the same activity of a NS4B NBM polypeptide in the absence of a candidate agent.

The portion of the protein employed in such screening may be free in solution, affixed to an abiotic or biotic substrate (e.g. borne on a cell surface), or located intracellularly.

Assays may be performed in a cell free system, using NS4B NBM polypeptide that is in solution or immobilized in a solid support, or, in other embodiments, using a cell containing a NS4B NBM polypeptide within the cell or on its surface.

Assays for nucleotide binding are generally very well known in the art (for example, as described in Feig, Mol Endocrinol. 1987 February;1(2): 127-36; Sigal, Anticancer Drug Des. 1987 October;2(2):107-15; Colman, Adv Exp Med Biol. 1990;281:257-63; Ali, J Pharmacol Toxicol Methods. 1994 December;32(4):187-96; and Farr, Natl. Acad. Sci. USA. 1990 July 1; 87 (13): 5041-5045), and generally involve producing a nucleotide binding polypeptide bound to a solid support, incubating the polypeptide with a labeled nucleotide, washing the solid support, and determining if the nucleotide is associated with the solid support. Other assays may involve assays for nucleotide hydrolysis, which are also well known in the art (e.g., Wilkes, Biochem Biophys Res Commun. 2002 August 16;296(2):388-94; Krumins, Methods Enzymol. 2002;344:673-85; and Tisdale, Mol Biol Cell. 1999 June;10 (6):1837-49).

Assays for RNA binding are also well known in the art, and may be adapted for use in the subject methods. In many embodiments, subject polypeptide is contacted with a nucleotide (e.g., G, A, T or C) and candidate agent in the presence of RNA, and RNA binding to the polypeptide is evaluated. Exemplary assays for evaluating RNA binding are well known in the art (see, e.g., Blair et al, RNA.1998 4:215-225; Gallinari et al, J Virol. 1998 72:6758-69; Cheng et al, J Virol. 1999 73:7044-9). A subject RNA binding assay may employ any RNA, although an RNA derived from the genome of a virus containing an nucleotide-binding NS4B protein (e.g., an HCV genome or any NS4B-binding fragment thereof) may be used.

A variety of different test compounds may be screened using the above methods. Test compounds encompass numerous chemical classes, though typically they are organic molecules, preferably small organic compounds having a molecular weight of more than 50 and less than about 2,500 daltons. Test compounds comprise functional groups necessary for structural interaction with proteins, particularly hydrogen bonding, and typically include at least an amine, carbonyl, hydroxyl or carboxyl group, preferably at least two of the functional chemical groups. The test compounds often comprise cyclical carbon or heterocyclic structures and/or aromatic or polyaromatic structures substituted with one or more of the above functional groups. Test compounds are also found among biomolecules including peptides, saccharides, fatty acids, steroids, purines, pyrimidines, derivatives, structural analogs or combinations thereof.

Test compounds may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In particular, candidate agents that are nucleotide variants, e.g., variants of nucleotides, nucleosides, ribonucleotides, etc., such as dGTP, dATP, dTTP and dCTP or variants thereof are of particular use. For example, non-hydrolysable nucleotides, GTPγS, GppNHp, GMPPCP, 5'-adenylylimido-diphosphate, guanosine 5'-3-O-(thio)triphosphate, 5'-O-(thio)triphosphate and adenosine 5'-(βγ-imino)triphosphate, Gpp(NH)p, etc may be used. In some variants, the ribose moiety can be replaced with carbocyclics, smaller and larger rings, conformationally constrained rings, and acyclics. Conformational constraints such as fused cyclopropane and cyclopentane rings in place of ribose can also be built into the ribose rings of nucleoside and nucleotide ligands. Phosphate analogs may also be used. Further examples of nucleotide variants may be found in Jacobson et al., (Nucleic Acids. 2001 20:333-41) and Plunkett et al., (Cancer Chemother Biol Response Modif. 2001;19:21-45).

Also of particular interest are antibodies, particularly neutralizing antibodies or phage display antibodies, that bind to a NS4B NBM of a polypeptide and reduce a nucleotide binding activity of the polypeptide (e.g., reduce affinity of the polypeptide to a nucleotide, or reduce nucleosidase activity).

In particular embodiments, agents that bind to the NS4B NBM but not NBMs from host (e.g. human) proteins are desirable because they may inhibit GTP binding activity of the NS4B, but do not inhibit GTP binding activity of human proteins. Such agents, e.g., monoclonal antibodies, phage display peptides, etc, may be identified using a number of approaches. In one embodiment, monoclonal antibodies that specifically bind a NS4B NBM are produced and tested against a number of host protein NBMs, or a protein having a consensus host NBM. In another embodiment, a phage display library is screened for phage that bind to a NS4B NBM but not host NBMs, or a consensus thereof.

An agent, which may be identified using the above assays, may be assayed in a variety of cellular and animal models of HCV, as discussed below.

In vitro Assays

The subject assays may include contacting a cell infected with HCV i.e., HCV or model thereof (e.g., an HCV subgenomic replicon; Lim, Virology. 2002 303(1):79-99), with an agent, and determining the effect of the agent on replication of HCV.

In general, an anti-HCV agent identified using the subject methods will reduce HCV replication by up to 50%, up to about 80%, up to about 90% or up to about 95% or more, using a standard replicon colony formation assay, as compared to controls in the absence of an agent.

In some embodiments of the invention an agent is contacted with a cell that is already infected with HCV, or, in certain other embodiments, an agent is contacted with a cell before its infection with HCV. In these embodiments, the antiviral agent may be administered as a prophylactic, e.g., to increase the viability of a cell and provide "protection" of a cell against a future viral infection.

In vivo Assays

In certain embodiments, the subject assays include, for example, administering an agent identified using the above method to a non-human animal model for HCV. Many such animal models using mammals, especially of mouse, monkeys, rats, cats, dogs, guinea pigs, etc., are known to one of skill in the art. Mouse models, in particular the mouse models for HCV, described in PCT publication WO01/67854, may be used. Other models include those described in WO 99/16307 and Galun et a. *J. Infect. Dis.* 172:25-30 (1995), describing transplantation of HCV-infected human hepatocytes into liver of immunodeficient mice; Bronowicki et al. *Hepatology* 28:211-8 (1998), describing intraperitoneal injection of HCV-infected hematopoietic cells into SCID mice; and Lerta et al. *Hepatology* 28(4Pt2):498A (1998), describing mice transgenic for the HCV genome.

In many embodiments, upon administration of a subject agent, a symptom (e.g. viability of pathogen infected cells, lesions, bleeding, bruising, titer, ALT, the number of infected cells) of the pathogen exhibited by the animal is reduced up to 20%, up to 50%, up to 70%, up to 80%, up to 90%, up to 95%, up to 98%, and even up to 99% or 99.5% as compared to an animal that is not administered a subject agent. In other embodiments, upon administration of a subject agent, a symptom (e.g. CD4 count, ALT or HAAT activity, etc.) of the pathogen exhibited by the animal is increased up to 20%, up to 50%, up to 70%, up to 80%, up to 90%, up to 95%, up to 98%, and even up to 99% or 99.5%, as compared to an animal that is not administered a subject agent.

In many embodiment, a blood sample is taken from the animal and tested for the level of a blood product, such as a virus, cell, a protein, or a molecule (e.g. viral titer, viral genome, viral mRNA, CD4 countor HAAT activity etc.). In other embodiments, a sample of tissue is taken from the test animal and symptoms (e.g. cell death, lesions, viral titer etc) are measured.

Immune Response-Stimulating Compositions

Virus particles containing the subject NS4B NBM polynucleotides, particularly those polynucleotides encoding variants that have altered (e.g. increased or reduced, including abolished and constitutively active) nucleotide binding activity may also be used in a composition for stimulating an immune response, e.g., to elicit anti-HCV antibodies, to elicit a T cell-specific immune response. Such compositions can be used as a vaccine for HCV, e.g., as a prophylactic (i.e., to prevent infection) or therapeutic (to treat HCV following infection) vaccine. In other words, a subject vaccine may contain a NS4B NBM polynucleotide that encodes an NS4B NBM polypeptide that is, for example, defective in that it cannot bind nucleotide, or constitutively active. Such polynucleotides may contain an NS4B NBM polypeptide in addition to or in replacement of an endogenous NS4B NBM. Vaccines containing such nucleotides can usually replicate in a subject.

The vaccines may be administered in conjunction, i.e., mixed with or serially with other antigens and immunoregulatory agents, for example, immunoglobulins, cytokines, lymphokines, and chemokines, including but not limited to cytokines such as IL-2, modified IL-2, GM-CSF, IL-12, .gamma.-interferon, IP-10, MIP1β, FLP-3, ribavirin and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the HCV particles may be conjugated to a bacterial toxoid, such as toxoid from diphtheria, tetanus, cholera, etc.

Such compositions may be administered with adjuvants, which adjuvants are well known in the art.

Utility

The invention finds use in identifying anti-HCV drugs, or providing an anti-HCV vaccine, for the treatment HCV infection in a subject. In this context, treatment can involve reduction of HCV load in the infected subject (e.g., reduction of viral load or viral titer). The invention also contemplates preventing or reducing the risk of symptoms or disease of infection by a HCV in a susceptible subject. Examples of subjects in this latter category include, but are not necessarily limited to, organ transplant recipients (e.g., liver transplants, bone marrow or other immune cell transplants, and the like). Of particular interest is treatment of a subject having a chronic HCV infection, including those undergoing liver transplant as therapy so as to clear the HCV infection and reduce the risk of re-infection of the donor liver and immunocompromised or otherwise immune deficient subjects (e.g., due to autoimmune disease, AIDS, genetic defect, and the like).

Specific exemplary intracellular pathogen infections contemplated for treatment according to the invention include, but are not necessarily limited to, those infections associated with hepatitis C virus (HCV, including HCV genotypes 1, 2, 3, and the like).

The pathogen may be present in a virulent, latent, or attenuated form, or in a combination of those forms. The subject may be symptomatic or asymptomatic.

In one embodiment, a liver that is to be transplanted into a patient is treated with a subject agent prior to transplantation.

In another embodiment, the liver of an infected patient is removed from the patient, treated with a subject agent, and placed back into the patient.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The agents and vaccines of the invention can be administered as a sole active agent, in combination (together or serially) with (i.e., as a "cocktail" with) one or more other anti-HCV agent, such as, for example, ribavirn and/or ribavirin derivatives, IFN-α (e.g., IFN-α2a, IFN-α2b, PEG-IFN-α2a, PEG-IFN-α2b, consensus IFN), reverse transcriptase inhibitors (e.g., a dideoxynucleoside including AZT, ddI, ddC, d4T, 3TO, FTC, DAPD, 1592U89 or CS92); and other agents such as 9-(2-hydroxyethoxymethyl) guanine (acyclovir), ganciclovir or penciclovir, interleukin II, or in conjunction with other immune modulation agents including bone marrow or lymphocyte transplants or other medications such as levamisol or thymosin which would increase lymphocyte numbers and/or function as is appropriate.

Since modulators (i.e., inhibitors and activators) of nucleotide binding activities of nucleotide binding protein are generally well known, e.g., the non-hydrolysable nucleotides discussed above, or may be discovered using the screening methods described above, the invention provides a method of modulating the activity of a NS4B NBM polypeptide. In general, this method involves contacting a NS4B NBM polypeptide with a modulator of a nucleotide binding activity of the peptide to modulate the activity of the polypeptide.

Further, the invention provides methods of inhibiting HCV replication in a cell. In general, these methods involve contacting a cell infected with HCV (including models for HCV) with an inhibitor of HCV NSB4 nucleotide binding (e.g., an agent that blocks nucleotide binding to the NBM of NS4B or that competes for nucleotide binding with NBM (e.g., a transdominant NS4B NBM polypeptide having enhanced nucleotide binding relative to the NS4B NBM of the HCV genome of the infected cell), to reduce HCV replication in the cell. In many embodiments, recombinant HCV containing a nucleic acid encoding a NS4B polynucleotide with altered nucleotide binding activity (e.g., a transdominant variant) may be used to reduce HCV replication in a cell. As discussed above, this method may be practiced in many cell types, including cells in vitro and in vivo.

Kits

Also provided by the subject intention are kits for practicing the subject methods, as described above. The subject kits at least include one or more of: a recombinant NS4B NBM polypeptide or a nucleic acid encoding the same; a recombinant NS4B NBM polypeptide that has reduced nucleotide binding activity as compared to a native NS4B, or a nucleic acid encoding the same; or virus particles containing any of the subject compositions. Other optional components of the kit include: adjuvant, carrier, syringes, other anti-viral drugs, etc. Any nucleic acids in the kit may also have restrictions sites, multiple cloning sites, primer sites, etc to facilitate their ligation to other plasmids. The various components of the kit may be present in separate containers or certain compatible components may be precombined into a single container, as desired. In many embodiments, kits with unit doses of the active agent, e.g. in oral or injectable doses, are provided.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Materials and Methods

Cell Cultures. Cell monolayers of the human hepatoma cell line Huh-7 were routinely grown in complete medium consisting of equal volumes of Dulbecco's modified minimal essential medium (DMEM, Gibco) and Roswell Park Memorial Institute 1640 (RPMI1640, Gibco), supplemented with 1% L-glutamine (Gibco), 1% penicillin, 1% streptomycin and 10% fetal bovine serum (FBS). Cell lines were passaged twice weekly after treatment with 0.05% trypsin-0.02% EDTA and seeding at a dilution of 1:10.

Antibodies. A Rabbit polyclonal antibody against GFP and an anti-rabbit secondary antibody were purchased from Molecular Probes (Oregon). A monoclonal antibody against GST was purchased from Cell Signaling Technology (Massachusetts).

Plasmids. Standard recombinant DNA technology was used to construct and purify all plasmids. All regions that were amplified by PCR were analyzed by automated DNA sequencing. Plasmid DNAs were prepared from large-scale bacterial cultures and purified by a Maxiprep kit (Marligen Biosciences). Restriction enzymes were purchased from New England Bio Labs (Massachusetts).

The plasmid Bart79I was described previously. Briefly, it was made by PCR mutagenesis (9) of HCVrep1bBartMan/AvaII (3) such that nucleotide 5336 was changed from a G to T resulting in a change in NS5A codon 1179 from serine to isoleucine. This mutation results in a dramatic increase in replication efficiency of the HCV subgenomic replicon (3). The NS4B NBM mutants of Bart79I (numbers represent the amino acid position relative to amino acid number 1 of NS4B), G129V ("GV"), I131N ("IN"), K135S ("KS") and K135R ("KR") were generated by site-directed mutagenesis using a PCR-based method. Briefly, complementary primers (a forward primer-1, 3, 5 or 7 with primer 10 or a reverse primer 2, 4, 6 or 8 with primer 9, Table 1) and the enzyme Platinum Pfx (Invitrogen) were used to generate by PCR two DNA fragments with overlapping ends containing the mutation. These ends were annealed to allow 3' extension of the complementary strand using the 3' overlap of each strand as a primer. The product was then further amplified by PCR using primers 9 and 10 (Table 1). The PCR products and the vector Bart79I were cut with SspI and MluI followed by ligation with T4 DNA ligase (Invitrogen) and transformation into chemically competent *E. Coli* (One Shot Top10 competent cells-Invitrogen).

TABLE 1 oligonucleotide primers.

| # | Primer name* | Sequence (5' → 3') |
|---|---|---|
| 1 | G129V-for | CGCTGGAGCGGCTGTTGTCAGCATAGGCCTTGGGAAGG (SEQ ID NO:25) |
| 2 | G129 V-rev | CCTTCCCAAGGCCTATGCTGACAACAGCCGCTCCAGCG (SEQ ID NO:26) |
| 3 | I131N-for | GCGGCTGTTGGCAGCAACGGCCTTGGGAAGGTGC (SEQ ID NO:27) |
| 4 | I131N-rev | GCACCTTCCCAAGGCCGTTGCTGCCAACAGCCGC (SEQ ID NO:28) |
| 5 | K135S-for | GCAGCATAGGCCTTGGGAGTGTGCTTGTGGATATTTTGG (SEQ ID NO:29) |
| 6 | K135S-rev | CCAAAATATCCACAAGCACACTCCCAAGGCCTATGCTGC (SEQ ID NO:30) |
| 7 | K135R-for | GCAGCATAGGCCTTGGGAGGGTGCTTGTGGATATTTTGG (SEQ ID NO:31) |
| 8 | K135R-rev | CCAAAATATCCACAAGCACCCTCCCAAGGCCTATGCTGC (SEQ ID NO:32) |
| 9 | 3800sp-for | GTCATTGTGGGCAGGATCATCTTGTCCGGAAAGCC (SEQ ID NO:33) |
| 10 | 5Right-rev | GTGACCCAACCAGGTATATTGATTGAGCCCGACCAGGAATGTGACC (SEQ ID NO:34) |
| 11 | NcoI-4B-for | CAGCCATGGCCTCACACCTCCCTTACATCG (SEQ ID NO:35) |
| 12 | 4B-NcoI-rev | CATGCCATGGCGCATGGCGTGGAGCAGTCCTCG (SEQ ID NO:36) |
| 13 | Attb-TEV-4B-for | GGGGACAAGTTTGTACAAAAAAGCAGGCTTCGAAAACCTGTATTTTCAGGGCGCCTCACACCTCCCTTACATCGAAC (SEQ ID NO:37) |

TABLE 1-continued oligonucleotide primers.

| # | Primer name* | Sequence (5' → 3') |
|---|---|---|
| 14 | 4B-stop-attb-rev | GGGGACCACTTTGTACAAGAAAGCTGGGTTTAGCATGGCGTGGAGCAGTCCTCG (SEQ ID NO:38) |
| 15 | 4Left-for | AGAGCGTCTTTACAGGCCTCACCCACATAGACGCCCATTTCTTGTCCCAG (SEQ ID NO:39) |
| 16 | 4Right-rev | AGGGCGCCAGGGGAGAGGATAGCAGGGAGTAGGTTAACCAGGTCCTCGG (SEQ ID NO:40) |

The plasmid PEF-NS4B-GFP was constructed in a two step cloning procedure as follows. A PCR fragment of NS4B amplified from Bart79I with forward and reverse primers containing NcoI restriction sites (primers 11, 12, Table 1) was digested with NcoI and ligated with NcoI-digested T7GFP plasmid (6) to generate the plasmid T7NS4BGFP. The plasmid T7NS4BGFP was digested with BglII-KpnI and the fragment corresponding to NS4BGFP was inserted into a BamHI-KpnI digested PEF6myc-HisA (Invitrogen) to yield PEF-NS4B-GFP. To obtain the plasmids with mutations in the NBM in NS4B, G129V, I131 N, K135S, and K135R (see above) were digested with NdeI-HpaI and the fragment corresponding to the mutated NBM was inserted into NdeI-HpaI-digested PEF-NS4BGFP.

The plasmids GST-NS4B and the corresponding NBM mutants were generated by using the Gateway technology (Invitrogen) according to the manufacturer's protocol. In brief, a forward primer introducing a recombination site (attb) and a TEV protease cleavage site (primer 13, Table 1) and a reverse primer introducing a second recombination site and a stop codon (primer 14, Table 1) were used to generate a PCR product of WT or mutant NS4B flanked by the two recombination sites. This product was first introduced into a donor vector (pDonor 201) from which it was transferred to the destination vector, pDEST15, to yield GST-NS4B by a two-step recombination procedure. 5AGFP plasmid was described previously (6).

Infection/transfection. A vaccinia virus that expresses the T7 RNA polymerase (T7RNAP) was used to infect Huh7 cells. Following 45 minutes incubation at 37° C. the cells were washed twice with Optimem (Invitrogen) and subjected to transfection with the appropriate construct using Lipofectamine 2000 (Invitrogen) according to the manufacturer's protocol. The cells were supplemented with growth medium and incubated for 5 hours at 37° C.

GTP binding assay. Photoaffinity labeling of NS4B-GFP in membrane preparations with $^{32}$P-labeled GTP-γ-4-azidoanilide ([$^{32}$P]GTPγAA) (38Ci/mmol) (Affinity Labeling Technologies, Inc.) was carried out essentially as described (13). Cellular membrane preparations were prepared from vaccinia virus infected/transfected Huh-7 cells. Following infection/transfection the cells were collected by trypsinization, washed once with PBS and resuspended in HME buffer (20 mM HEPES pH 7.4, 1 mM EDTA, 2 mM $MgCl_2$) that was supplemented with PMSF to a final concentration of 1 mM and protease inhibitor cocktail (Sigma). The cells were lysed by two cycles of freeze-thaw in dry ice-ethanol and then passaged through a 27.5 G needle 10 times to facilitate complete brake down of the cell membranes. Nuclei were removed by centrifugation at 1000 rpm for 10 min and the post nuclear supernatant was subjected to ultra centrifugation at 100,000×g for 30 minutes to obtain the membrane preparation. All steps were done at 4° C. One hundred and fifty micrograms of total membrane protein were resuspended in 20 mM NABEPES, pH 7.4. The assay mixture containing 30 μl membrane preparation, 30 μl of 3× binding buffer (30 mM Na HEPES, pH 7.4, 100 mM NaCl, 0.1 mM EDTA, 10 mM MgCl2) and 30 μl of [$\gamma^{32}$P]GTPγAA (total of 15 μCi) was incubated for 1 hour at 30° C. in the dark. Samples were then irradiated with UV light at a 3 cm distance for 1 minute (2000 μwatts, 254 nm, UVS-28, UV Products) to allow covalent attachment of the bound radio-labeled guanine nucleotide. Unbound nucleotides were removed by ultra centrifugation for 10 min at 100,000×g and the membranes were resuspended in 1× binding buffer containing 2 mM DTT (for inactivation of the unbound material) and irradiated on ice for an additional 3 minutes with UV light.

Immunoprecipitation of labeled NS4B-GFP. To identify the [$\gamma^{32}$P]GTPγAA-labeled NS4B-GFP, membrane preparations were incubated in 1 ml of TDB buffer (2.5% Triton X-100, 25 mM TEA-Cl, pH 8.6, 20 mM NaCl, 0.5M EDTA and 0.2% NaN3) followed by ultracentrifugation at 100,000×g for 10 minutes. The supernatants were incubated overnight with a rabbit polyclonal antibody directed against GFP (Molecular Probes), and Protein A-Sepharose (Amersham Biosciences). Following three washes in NET buffer (150 mM NaCl, 0.5 mM EDTA and 50 mM Tris-Hcl, pH 8.0) immunoprecipitates were solubilized in sample buffer and analyzed by SDS-polyacrylamide gel electrophoresis (SDS-PAGE), and autoradiography. Nitrocellulose membranes were also subjected to western analysis with mouse anti-GFP antibodies (Roche), and horseradish peroxidase-conjugated donkey anti mouse IgG, followed by chemiluminescence (Amersham) development.

Transfection. DNA constructs were transfected into Huh7 cells using Lipofectamine 2000 (Invitrogen, USA) according to the manufacturer's protocol.

Fluorescence microscopy. Cells expressing GFP fusion proteins were fixed in 4% formaldehyde eighteen hours post transfection and mounted using mowiol mounting media. Fluorescence images were captured using a Nikon E600 fluorescence microscope equipped with a SPOT digital camera and the Openlab (Improvision, UK) image acquisition software.

Expression and purification of wild type and mutants of GST-NS4B. Proteins were expressed and purified as previously reported (30). Overnight cultures of *E. coli* transformed with parental of recombinant pDEST15 plasmids were diluted 1:100 in 400 ml of fresh medium and grown at 37° C. to an OD of 0.6. Isopropyl-β-D-thiogalactopyranoside (IPTG-Invitrogen) was then added to a final concentration of 0.1 mM. After 2 hours growth at room temperature cells were pelleted and resuspended in 25 ml lysis buffer (PBS, pH 7.3, 1% Triton X-100 (J. T. Baker), 100 units/ml DNAse (Sigma), 100 μg/ml Lyzosyme (Sigma), Protease Inhibitor cocktail (Sigma), 1 mM phenylmethylsulfonylfluorid (PMSF) (Sigma), and 2 mM $MgCl_2$). After 15 minutes incubation on ice, cells were lysed by one cycle in a French Press at a pressure of 10,000 psi for 1 minute, followed by centrifugation at 12,000×g for 5 minutes at 4° C. The supernatant was mixed at 4° C. on a rotating platform with 200 μl 50% glutathione-agarose beads (Sigma). Beads were then washed three times with PBS. GST-NS4B was eluted by 10 minutes incubation at room temperature in 100 μl elution buffer (50 mM Tris-HCl, pH 8.0, 10 mM reduced glutathione, and 0.1% Triton X-100). Elution was repeated twice. Glycerol was added to the pooled eluates at a final concentration of 20% and stored at −20° C. until use as described below. Expression and purification were monitored by SDS-PAGE followed by Coomassie-stain or western blot analysis with an anti-GST antibody. We estimate the maximum amount of non-GST containing protein to be <5%. In addition to the expected full-length GST-NS4B band at 58 kDa, some faster migrating GST-containing bands were also detected. The latter appeared to be the result of premature termination as their size correlated with the position of codons poorly recognized by standard *E. coli* strains and they were found to significantly decrease by the addition of appropriate tRNAs in an in vitro expression system (Rapid Translation System, Roche) (T. Danieli, unpublished data). Typical final yields were five micrograms of total protein per 100 ml bacterial culture. Of note, there were no differences in yield or purity of the NBM mutants compared to wild type GST-NS4B.

GTPase assays. The standard GTPase assay was performed as previously described (25). Half a microgram of purified protein was incubated in a 30 μl reaction mixture containing 20 mM HEPES/KOH, pH 6.8, 10 mM $MgCl_2$, 2 mM DTT, 40 μM cold GTP (Promega) and 15 μci/ml [$\gamma^{32}$P]GTP (5000 Ci/mmol Amersham Biosciences). Serial aliquots were collected at different incubation time intervals (5, 15, 30, 45 and 60 minutes) while the reaction was performed at 37° C. The reaction was terminated on ice by the addition of EDTA to a final concentration of 5 mM. Half a microliter aliquots were then spotted onto polyethyleneimine cellulose (PEI)-coated thin layer chromatography (TLC) plates (Merck). Plates were developed in 0.15 M LiCl-0.15M Formic acid (pH 3.5) in a TLC chamber, dried, and subjected to autoradiography and quantitative phosphorimager analysis.

In-vitro RNA transcription. Plasmid DNA of wild type HCV replicon (Bart79I) and replicons harboring the various NS4B NBM mutations were linearized using ScaI and treated with Proteinase K followed by phenol:chloroform extraction and precipitation with ethanol. The DNA was resuspended in Rnase-free water to a final concentration of 1 μg/μl. Four micrograms DNA were used as template for transcription using the Ribomax® RNA production kit (Promega) according to the manufacturer's protocol. The template DNA was digested by the addition of 5 units of RQ1 DNase (Promega) and 15 minutes incubation at 37° C. The unincorporated ribonucleotides were removed by size exclusion using a Micro Bio-Spin® P-30 column (Bio-Rad) and the transcribed RNA was extracted with phenol:chloroform followed by precipitation in ethanol. The RNA pellet was washed with 70% ethanol and resuspended in $H_2O$. Determination of the RNA concentration was performed by measurement of the optical density at 260 nm. The integrity of the RNA and its concentration were confirmed by 1% agarose gel electrophoresis and ethidium bromide staining.

Colony formation assays. The standard replicon colony formation assay was performed as previously described (3, 6). Briefly, subconfluent Huh-7 cells were trypsinized and collected by centrifugation at 700×g for 5 minutes. The cells were then washed three times in ice-cold RNase-free PBS (BioWhitaker), and resuspended at $1\times10^7$ cells/ml in PBS.

Five micrograms of in-vitro transcribed RNA were mixed with 0.4 ml of washed Huh-7 cells in a 2-mm gap cuvette (BTX) and immediately pulsed (0.68 kV, 5×99 µs) using a BTX-830 Electroporator. After 10 minutes recovery at room temperature, pulsed cells were then diluted into 10 ml pre-warmed growth medium. Cells were plated in 10 cc tissue culture dishes at different densities ($4\times10^6$, $4\times10^5$, $8\times10^4$ and $4\times10^4$, cells per dish) to permit accurate colony counting. Twenty-four hours post electroporation, the cells were supplemented with plain Huh-7 to a final density of $1\times10^6$ cells/plate. Following an additional 24 hours, the selecting drug, G418 (Invitrogen) was added to the medium to a final concentration of 1 mg/ml. Growth medium supplemented with G-418 was replaced every 4 days for 3 weeks. The plates were then washed twice with PBS, incubated in 1% crystal violet made in 20% ethanol for 5 minutes, followed by 3 washes with $H_2O$ to facilitate colony counting. The G-418 transduction efficiency was calculated based on the number of G418 resistant colonies relative to the number of Huh-7 cells plated after electroporation. Results were expressed as colony forming units (number of colonies per µg transfected RNA) of each mutant relative to the wild type replicon.

RNA extraction, RT-PCR amplification and sequencing. Several G418-resistant clones were isolated from colony formation assays performed with the replicon harboring the GV mutation. Total cellular RNA of individual clones was extracted using TRIZOL reagent (Invitrogen, Calif.) according to the manufacturer's protocol. Reverse transcriptase reaction and PCR amplification were performed using the Superscript One-Step RT-PCR kit (Invitrogen, Calif.) according to the kit's protocol. Briefly, the amplification reaction included 1 µg of total RNA as template and 10 pmol of each primer. Two sets of primers (4Left-for with 4Right-rev and 3800-for with 4Right-rev, Table 1) were used to amplify 1 kb and 650 bp segments, respectively, each containing the NBM region. Performing two independent amplification reactions for each clone provided further confirmation of the sequencing results. The RT reaction was performed at 50° C. for 30 minutes followed by incubation at 95° C. for 2 min. The DNA was amplified by 28 cycles of 95° C. for 15 sec, 60° C. for 30 sec and 68° C. for 1 min. A final elongation step was performed at 68° C. for 10 min. The PCR products were purified from agarose gels using Ultra clean 15 DNA purification kit (MoBio, CA) and sent for automatic sequencing on an ABI Prism 377 DNA sequencer (Sequetech, CA).

Protein assays. Concentrations of purified protein and protein content in membrane preparations were determined by the Bradford dye binding procedure using a Bio-Rad (Richmond, Calif.) protein assay kit.

RNA binding assay. 1 µg of purified protein was incubated for an hour at 37° C. in a 50 µl reaction mixture containing $^{32}P$-labeled in vitro transcribed HCV RNA (prepared by using Sca I-linearized Bart79I plasmid (wild type HCV replicon (3)) as template, T7 RNA polymerase, and Riboprobe®/Promega, according to the manufacturer's protocol), binding buffer (10 mM DTT, 10 mM Na HEPES (pH 7.4), 33 mM NaCl, 0.1 mM EDTA, 10 mM MgCl2) and 5 mM of either GTP-γ-S or GDP (Sigma). 50 µl of tRNA pre-coated glutathione-agarose beads (Sigma) were then added, followed by 1 hour incubation at 4° C. to allow binding of GST to the beads. Samples were then washed three times in the binding buffer (in the absence of nucleotides). Aliquots were finally subjected to liquid scintillation counting for measuring bound RNA. Control incubations performed with reaction mixture prepared as above but with omission of T7 RNA polymerase were run in parallel and used for background subtraction.

Example 1

NS4B Contains a Nucleotide Binding Motif

Inspection of the NS4B primary sequence revealed the presence of a nucleotide binding motif (NBM) within the middle of NS4B. This motif consists of a set of conserved amino acids found in both the GTP-binding members of the G-protein family, as well as in the superfamily of viral proteins with nucleotide-binding domains. The most highly-conserved elements within these nucleotide-binding domains are the so-called A motif and B motif (FIG. 1, A and B). Because binding and hydrolysis of nucleotides mediate a variety of critical signaling, membrane trafficking, and membrane fusion events, we hypothesized that the NBM within NS4B may similarly be important for NS4B's role in HCV RNA replication.

Example 2

NS4B Binds GTP

To determine the properties associated with the wild type and mutated versions of NS4B's NBM, a plasmid was constructed, termed NS4B-GFP, which encodes a NS4B protein with a C-terminal, in frame green fluorescent protein (GFP) tag. The latter allows for visualization in live cells and provides a convenient epitope outside of any future field of mutagenesis within NS4B. Importantly, GFP fusions to NS4B have been previously reported to have no difference in intracellular localization patterns from those described for wild type NS4B.

To test the hypothesis that NS4B can bind GTP, GTP-binding experiments using Huh-7 cells infected with a T7RNAP-expressing vaccinia virus and transfected with plasmids encoding NS4B-GFP, GFP, or mock transfected, were performed. Membrane preparations were prepared and aliquots incubated with $^{32}P$-labeled GTP-γ-4-azidoanilide (a UV-photoactivatable non-hydrolyzable GTP analog) essentially as previously described. Following a brief pulse of UV-irradiation to activate covalent attachment of any bound GTP, pelleted membranes were washed and subjected to immunoprecipitation with a rabbit anti-GFP antibody, SDS-PAGE, transfer to nitrocellulose, autoradiography and western blot.

Figures 2A, 2B:
FIGS. 2A and 2B display autoradiographs showing that HCV NS4B binds GTP. Membrane preparations from Huh-7 cells transfected with plasmids encoding NS4B-GFP (lanes 1 and 5), GFP (lanes 2 and 6), mock transfected (lanes 3 and 7) or transfected with 5A-GFP (lanes 4 and 8) were incubated with $^{32}$P-labeled photoactivatable GTP. Following one minute of UV-irradiation to activate covalent attachment of any bound GTP, samples were washed and subjected to immunoprecipitation with a rabbit anti-GFP antibody, SDS-PAGE, and autoradiography (2A). Aliquots of the immunoprecipitates were also analyzed by western blot probed with a mouse anti-GFP antibody followed by chemiluminescence detection (2B). Molecular weight markers (in kDa) are indicated on the right.

As shown in FIG. 2A, NS4B-GFP, but not GFP, was specifically labeled with GTP (FIG. 2A, lanes 1 vs. 2). Western analysis with an antibody to GFP of the immunoprecipitates revealed comparable expression levels of the two proteins (FIG. 2B, lanes 5 vs. 6). To provide another measure of the specificity of the observed labeling, assays were performed with plasmid 5A-GFP, which encodes for the first 31 amino acids of HCV NS5A fused in frame to the N-terminus of GFP. The resulting fusion protein thus contains, like NS4B, a potent membrane-targeting N-terminal amphipathic helix yet does not include a known nucleotide binding element. Essentially no GTP labeling of 5A-GFP was observed (FIG. 2A, lane 4) in spite of a larger amount of expressed protein (FIG. 2B, lanes 8 vs. 5). Labeling of 5A-GFP detectable only after extensive film exposure was used for background subtraction purposes in subsequent quantitative analyses. This is the first demonstration that NS4B has GTP-binding activity. In addition, these results indicate that such binding activity is preserved when NS4B is expressed in the form of a fusion protein.

Similarly, other amino acids of the NS4B NBM may be changed to impair HCV replication. For example, e.g., altering the "D" of the "DAAA" motif to L, and altering the "F" and "T" amino acids of the NS4B NBM to A also result in impaired HCV replication.

Figures 3A, 3B, 3C:
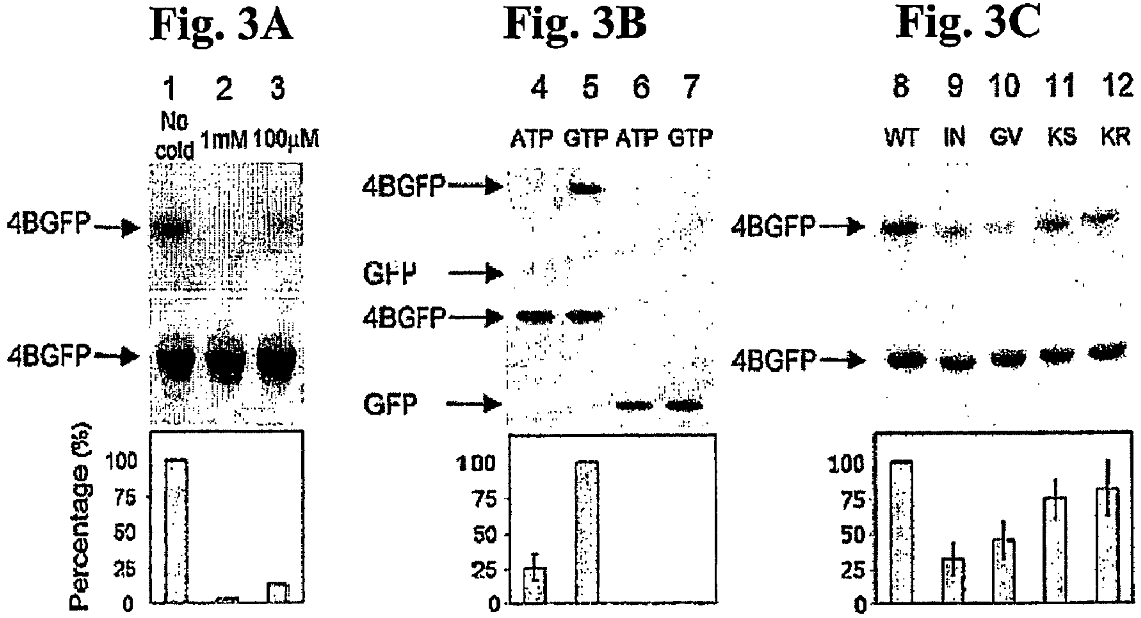
FIGS. 3A-3C displays results showing that the NS4B NBM is specific for GTP and sensitive to genetic mutation.

The specificity of NS4B's GTP binding was further evaluated by performing binding experiments in the presence of excess unlabeled ligand. Membrane aliquots of Huh-7 cells expressing NS4B-GFP were incubated with $^{32}$P-labeled GTP analog as described above, except that cold GTPγS was added to the incubation mixture. As shown in FIG. 3A, binding of labeled GTP was progressively decreased in the presence of increasing concentrations of the cold competitor nucleotide (FIG. 3A, top panel, lane 1 vs. lanes 2 and 3).

Binding assays were performed using Huh-7 cells expressing NS4B-GFP as in FIG. 2. Membrane aliquots were incubated with equal concentrations of $^{32}$P-labeled ATP-γ4-azidoanilide or GTP-γ-4-azidoanilide analog followed by immunoprecipitation. As shown in FIG. 3B, although NS4B can bind ATP, this appears to be significantly less efficient than GTP binding (FIG. 3B, top panel, lane 4 vs. 5). Again, no labeling of the control GFP was detected with either ATP or GTP (FIG. 3B, top panel, lanes 6 and 7).

Example 3

Mutation of NS4B's NBM Impairs GTP Binding

To test whether mutations within the NS4B NBM can impair GTP binding four mutants each harboring a single amino acid mutation within the NS4B NBM (see FIG. 1C) were designed. Ile131 Asn (or "IN") has a single amino acid change at the $X_2$ position of the NS4B NBM, a position that has been shown to be critical for NBM function in other proteins. The Lys135Ser ("KS") and Lys135Arg ("KR") mutants both have a single amino acid change at position 135. The Gly129Val ("GV") is a single amino acid mutation at the highly conserved first position of the NBM A-motif consensus sequence. These mutations were introduced into NS4B-GFP and GTP binding assays were performed. As shown in the top panel of FIG. 3C, the GV and the IN NBM mutant proteins exhibited a two to three fold reduction in GTP binding on average compared to that of the wild type NS4B-GFP protein (lanes 10 and 9 vs. 8). In contrast, the KS and KR NBM mutants reduced GTP binding activity to a lesser degree (lanes 11 and 12 vs. 8). This was not simply the result of an obvious gross effect of the mutations on folding, as the apparent intracellular expression levels and distribution patterns of mutant and wild type proteins appeared identical by fluorescence microscopy (FIG. 4). Moreover, western analysis with an anti-GFP antibody of the immunoprecipitates again revealed comparable levels of expression of these proteins (FIG. 3C).

Example 4

NS4B has GTPase Activity which is Mediated by the NBM

To test whether the NS4B NBM mediates GTP hydrolysis, wild type NS4B and the four NBM mutants were fused in frame with N-terminal Glutathione-S Transferase (GST) tags and assayed. The resultant fusion proteins, termed GST-NS4B, GST-NS4B-(IN), GST-NS4B-(GV), GST-NS4B-(KS) and GST-NS4B-(KR) were expressed in *E. coli* BL21 and purified with glutathione beads, as described. The purified proteins were then tested for their ability to hydrolyze GTP by a standard GTPase assay wherein release of phosphate from [γ$^{32}$P]GTP was monitored by quantitative thin-layer chromatography, essentially as previously described. Not only does NS4B have GTPase activity, but the latter is sensitive to disruption of the NBM (FIG. 5). Indeed, the targeted mutations could either partially (KS, KR) or nearly completely (GV, IN) abolish GTPase activity.

Example 5

Disrupting TN4B's NBM Inhibits HCV RNA Replication

To test whether the NS4B NBM is important for HCV replication, nucleic acids containing the above series of point mutations within the NBM were transferred into high efficiency HCV replicons (see FIG. 6B). The latter were then assayed in standard replicon colony formation assays, as previously described. A replicon carrying a lethal mutation in the active site of the viral polymerase (GDD→AAG), NS5B, was used as a negative control. The tested mutations had a variety of significant effects on replication (FIG. 7). While mutating the A-motif Lys to either Ser ("KS") or Arg ("KR") was associated with an intermediate level of replication (2% and 18% respectively), mutating the first Gly of the A motif to Val ("GV") dramatically inhibited replication with only rare colony formation. No colonies could be isolated when the A-motif Ile was changed to Asn ("IN"). The appearance of colonies on the GV plates provided us with the opportunity to perform reversion analyses. RNA was therefore extracted from the rare colonies isolated from such experiments, amplified by RT-PCR and sequenced. The sequence provided by these colonies has revealed the presence of only primary site revertants. This demonstrates the requirement of maintaining a functional NBM.

Efficient binding and hydrolysis of nucleotide by NS4B is therefore required for viral replication. To test the RNA-binding activity of NS4B, binding assays were performed with purified GST-4B or GST proteins and in vitro transcribed HCV RNA. To assess the dependence of RNA binding on the phosphorylation state of guanine nucleotide, reactions were also performed in the presence of GDP or GTP-γ-S. As shown in FIG. 8, the NS4B fusion protein bound significantly more HCV RNA than the GST control. In addition, the binding in the presence of GDP was dramatically increased over that observed in the presence of the non-hydrolyzable analog of GTP. Moreover, binding appears to be subject to regulation by guanyl nucleotide. Taken together, our results provide an intriguing new insight into the role of NS4B in the HCV lifecycle.

These results reveal that the NBM within NS4B represents an attractive new target for anti-HCV therapy. Because the amino acid sequence immediately adjacent to either side of the NBM region is highly conserved among HCV isolates yet very different from that contained in known host cell GTP-binding proteins, highly selective inhibitors can be readily screened for.

It is evident from the above results and discussion that the subject invention provides an important new tool for discovery of anti-HCV agents. In particular, the subject invention provides a system for identifying anti-HCV agents based on their ability to inhibit binding of a nucleotide, e.g., GTP, to an HCV-encoded NS4B polypeptide. As such, the subject methods and systems find use in a variety of different applications, including research, medical, therapeutic and other applications. Accordingly, the present invention represents a significant contribution to the art.

What is claimed is:

1. A method comprising:

contacting a hepatitis C virus (HCV) nucleotide binding NS4B protein with a candidate agent and HCV RNA; and determining an effect of said candidate agent on:

(i) GTPase activity or nucleotide binding of said NS4B protein; and (ii) HCV RNA binding of said NS4B protein.

2. The method of claim 1, wherein said candidate agent is a nucleotide analog.

3. The method of claim 2, wherein said nucleotide analog is a non-hydrolysable nucleotide.

4. The method of claim 1, further comprising determining an effect of said candidate agent on replication of HCV.

5. The method of claim 4, wherein said method comprises determining an effect of said candidate agent on HCV replication in a huh7 cell.

6. The method of claim 4, wherein said method comprises assaying said candidate agent on HCV replication in a liver cell line or primary liver cell.

* * * * *